US012754350B2

(12) United States Patent
Lee et al.

(10) Patent No.: US 12,754,350 B2
(45) Date of Patent: Oct. 6, 2026

(54) APPARATUS AND METHOD FOR MEASURING VISUAL ACUITY BY USING FOCUS-TUNABLE LENS

(71) Applicant: SAMSUNG ELECTRONICS CO., LTD., Suwon-si (KR)

(72) Inventors: Kyookeun Lee, Suwon-si (KR); Harry Edward Milton, Suwon-si (KR); Seungjae Lee, Suwon-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 508 days.

(21) Appl. No.: 17/874,958

(22) Filed: Jul. 27, 2022

(65) Prior Publication Data

US 2023/0036308 A1 Feb. 2, 2023

Related U.S. Application Data

(63) Continuation of application No. PCT/KR2022/010865, filed on Jul. 25, 2022.

(30) Foreign Application Priority Data

Jul. 27, 2021 (KR) ........................ 10-2021-0098785
Dec. 27, 2021 (KR) ........................ 10-2021-0188861

(51) Int. Cl.
*G02B 3/14* (2006.01)
*G02C 7/08* (2006.01)
*A61B 3/032* (2006.01)

(52) U.S. Cl.
CPC ............... *G02B 3/14* (2013.01); *G02C 7/085* (2013.01); *A61B 3/032* (2013.01)

(58) Field of Classification Search
CPC .... A61B 3/028; A61B 3/032; G02B 27/0172; G02B 3/14
See application file for complete search history.

(56) References Cited

U.S. PATENT DOCUMENTS 7,218,302 B2 * 5/2007 Ide .................... G02F 1/134309 345/94
10,327,630 B2 6/2019 Ohlendorf et al.
(Continued)

FOREIGN PATENT DOCUMENTS

EP 1411382 A2 4/2004
JP 11-318824 A 5/1998
(Continued)

OTHER PUBLICATIONS

International Search Report (PCT/ISA/220) dated Jul. 25, 2022, in App No. PCT/KR2022/009075.
(Continued)

*Primary Examiner* — Christopher Stanford
(74) *Attorney, Agent, or Firm* — Sughrue Mion, PLLC

(57) ABSTRACT

Provided are an apparatus and method for measuring a visual acuity (VA) by using a focus-tunable lens. The apparatus includes a display engine, an image combiner, a focus-tunable lens provided on a path of the light guided by the image combiner, an input device, and a processor configured to control the focus-tunable lens to assign different first and second optical powers to first and second lens regions, respectively, on a lens surface of the focus-tunable lens, control the display engine to display a VA measuring image through first and second output regions of the image combiner, control the input device to receive a user's input with respect to the VA measuring image, specify one optical power of the first and second optical powers based on the user's input, and determine a VA of a user based on the specified optical power.

15 Claims, 37 Drawing Sheets

(56) References Cited

U.S. PATENT DOCUMENTS

| | | | |
|---|---|---|---|
| 10,345,590 B2 | 7/2019 | Samec et al. | |
| 10,761,245 B2 | 9/2020 | Shibuya et al. | |
| 10,824,002 B2 * | 11/2020 | Imai | G02F 1/1343 |
| 11,256,096 B2 | 2/2022 | Samec et al. | |
| 11,442,332 B1 * | 9/2022 | Sprague | G02C 7/083 |
| 2012/0212399 A1 | 8/2012 | Border et al. | |
| 2012/0306848 A1 | 12/2012 | Lee | |
| 2017/0000329 A1 | 1/2017 | Samec et al. | |
| 2020/0003933 A1 | 1/2020 | Yadin et al. | |
| 2020/0038173 A1 | 2/2020 | Reedy et al. | |
| 2021/0315453 A1 | 10/2021 | Jeon | |
| 2024/0252036 A1 * | 8/2024 | Lussier | G02B 27/0075 |

FOREIGN PATENT DOCUMENTS

| | | | | |
|---|---|---|---|---|
| JP | 3373782 B2 | 2/2003 | | |
| KR | 10-2006-0024837 A | 3/2006 | | |
| KR | 10-0958704 B1 | 5/2010 | | |
| KR | 10-2017-0137726 A | 12/2017 | | |
| KR | 10-2019-0102536 A | 9/2019 | | |
| KR | 10-2170499 B1 | 10/2020 | | |
| KR | 10-2022-0140340 A | 10/2022 | | |
| WO | 2018/016390 A1 | 1/2018 | | |
| WO | WO-2020090811 A1 * | 5/2020 | | |
| WO | 2020/188104 A1 | 9/2020 | | |
| WO | WO-2020213723 A1 * | 10/2020 | | G02B 3/14 |

OTHER PUBLICATIONS

European Extended Search Report issued Oct. 11, 2024 by the E uropean P atent O ffice for E P P atent Application No. 22849831.7.

Communication issued Jun. 12, 2025 by the European Patent Office for EP Patent Application No. 22849831.7.

Communication dated Aug. 10, 2026 issued by the Korean Intellectual Property Office in counterpart Korean Application No. 10-2021-0188861.

* cited by examiner

APPARATUS AND METHOD FOR MEASURING VISUAL ACUITY BY USING FOCUS-TUNABLE LENS

CROSS-REFERENCE TO RELATED APPLICATIONS

This application is a bypass continuation application of International Application No. PCT/KR2022/010865, filed on Jul. 25, 2022, which is based on and claims the priority to Korean Patent Application No. 10-2021-0098785, filed on Jul. 27, 2021, and Korean Patent Application No. 10-2021-0188861 filed on Dec. 27, 2021, in the Korean Intellectual Property Office, the disclosures of which are incorporated by reference herein in their entireties.

BACKGROUND

1. Field

The present disclosure relates to an apparatus and method for measuring a visual acuity (VA) by using a focus-tunable lens.

2. Description of Related Art

A virtual reality (VR) device is a device allowing viewing of VR, and an augmented reality (AR) device is a device allowing viewing of AR. An example of a VR/AR device may include AR glasses. An image optical system of the VR/AR device includes an image generating device that generates an image and an optical system that transmits the generated image to the eyes of a user.

The image output from the image generating device (a projector, etc.) is emitted to the eyes through the optical system, allowing the user to see the image. With regard to a display using such an optical system, a focal distance of a virtual image may be, for example, infinite, such that, from among users using the VR/AR device, a user who uses glasses for correction of his/her visual acuity (VA) needs to use an additional means like a power clip. However, due to the inconvenience in use of the power clip, a VR/AR device providing a VA correction function for low-VA users by using a focus-tunable lens is being studied.

SUMMARY

According to an aspect of an embodiment, there is provided an apparatus configured to measure a visual acuity (VA) by a focus-tunable lens, the apparatus including a display engine configured to project light including a VA measuring image, an image combiner configured to guide the light projected from the display engine, the focus-tunable lens provided on a path of the light guided by the image combiner, an input device configured to receive a user's input with respect to the VA measuring image, a storage configured to store one or more instructions, and a processor configured to execute the one or more instructions to control the focus-tunable lens to assign a first optical power to a first lens region and a second optical power that is different from the first optical power to a second lens region, the first lens region and the second lens region being included in a lens surface of the focus-tunable lens, control the display engine to display the VA measuring image through a first output region and a second output region of the image combiner, which respectively correspond to the first lens region and the second lens region of the focus-tunable lens, control the input device to receive the user's input, specify one optical power of the first optical power and the second optical power based on the user's input, and determine a VA of a user based on the specified optical power.

A first VA measuring image displayed through the first output region and a second VA measuring image displayed through the second output region may be same images having same sizes.

The focus-tunable lens may include a first strip electrode liquid crystal lens and a second strip electrode liquid crystal lens including a first strip electrode array and a second strip electrode array, respectively, and the first strip electrode liquid crystal lens and the second strip electrode liquid crystal lens are provided such that the first strip electrode array and a second strip electrode array overlap each other orthogonally, and the processor may be further configured to apply a voltage to first strip electrodes included in the first strip electrode array and second strip electrodes included in the second strip electrode array such that the first lens region has the first optical power, and the first strip electrodes and the second strip electrodes pass by the first lens region, and apply a voltage to third strip electrodes included in the first strip electrode array and fourth strip electrodes included in the second strip electrode array such that the second lens region has the second optical power, and the third strip electrodes and the fourth strip electrodes pass by the second lens region.

The focus-tunable lens may include a pixel electrode liquid crystal lens including a pixel electrode array, and the processor may be further configured to apply a voltage to first pixel electrodes of the pixel electrode array, which pass by the first lens region, such that the first lens region has the first optical power, and apply a voltage to second pixel electrodes of the pixel electrode array, which pass by the second lens region, such that the second lens region has the second optical power.

The processor may be further configured to apply a voltage to electrodes of the focus-tunable lens such that the first optical power and the second optical power have spherical lens powers, when myopia or hyperopia of the user is measured.

The processor may be further configured to apply a voltage to electrodes of the focus-tunable lens such that the first optical power has a first cylindrical lens power with a first direction, placed on the lens surface of the focus-tunable lens, as an axial direction, and the second optical power has a second cylindrical lens power with a second direction, placed on the lens surface of the focus-tunable lens and orthogonal to the first direction, as an axial direction, when astigmatism of the user is measured.

The input device may include at least one of a gaze tracking sensor, a microphone, a button, and a gesture recognition sensor.

The image combiner may be further configured to guide the light projected from the display engine to a target region and project light of a real scene, and the focus-tunable lens may be provided on a path of the light guided from the image combiner to the target region.

The image combiner may include one of a waveguide, multiple mirrors, and a reflective mirror.

Information with respect to the measured VA of the user may be stored in the storage.

The apparatus may include an augmented reality (AR) device.

According to another aspect of an embodiment, there is provided a method of measuring a visual acuity (VA) by a focus-tunable lens, the method including assigning a first optical power to a first lens region and a second optical power that is different from the first optical power to a second lens region, the first lens region and the second lens region being included on a lens surface of the focus-tunable lens, displaying a VA measuring image through a first output region and a second output region of an image combiner, which respectively correspond to the first lens region and the second lens regions of the focus-tunable lens, receiving a first input of a user with respect to the VA measuring image, specifying one optical power of the first optical power and the second optical power based on the first input of the user, and determining a VA of the user based on the specified optical power.

A first VA measuring image displayed through the first output region and a second VA measuring image displayed through the second output region may be same images having same sizes.

The method may further include changing the first optical power and the second optical power based on the specified optical power and re-assigning the changed first optical power and the changed second optical power to the focus-tunable lens, displaying the VA measuring image and receiving a second input of the user, re-specifying one optical power of the changed first optical power and the changed second optical power based on the second input of the user, and determining the VA of the user based on the re-specified optical power.

The assigning of the first optical power and the second optical power to the focus-tunable lens may include applying a voltage to electrodes of the focus-tunable lens such that the first optical power and the second optical power have spherical lens powers based on measuring myopia or hyperopia of the user.

The assigning of the first optical power and the second optical power to the focus-tunable lens may include applying a voltage to electrodes of the focus-tunable lens such that the first optical power has a first cylindrical lens power with a first direction, placed on the lens surface of the focus-tunable lens, as an axial direction, and the second optical power has a second cylindrical lens power with a second direction, placed on the lens surface of the focus-tunable lens and orthogonal to the first direction, as an axial direction based on measuring astigmatism of the user, and the measuring of the VA of the user may include determining an astigmatism direction of the user based on an axial direction of the specified optical power.

The method may further include after changing the first direction in a range of 0 degree to 90 degree, assigning the changed first optical power and the second optical power to the focus-tunable lens, displaying the VA measuring image, receiving a third input of the user, re-specifying one optical power of the changed first optical power and the changed second optical powers based on the third input of the user, and re-measuring the VA of the user based on the re-specified optical power.

The first user input may be input by at least one of a gaze tracking sensor, a microphone, a button, and a gesture recognition sensor.

The method may further include storing the measured VA of the user in a storage of an apparatus.

According to another aspect of an embodiment, there is provided a computer-readable recording medium for executing a method of measuring a visual acuity (VA) by a focus-tunable lens on a computer, the method including assigning a first optical power to a first lens region and a second optical power that is different from the first optical power to a second lens region, the first lens region and the second lens region being included on a lens surface of the focus-tunable lens, displaying a VA measuring image through a first output region and a second output region of an image combiner, which respectively correspond to the first lens region and the second lens regions of the focus-tunable lens, receiving a first input of a user with respect to the VA measuring image, specifying one optical power of the first optical power and the second optical power based on the first input of the user, and determining a VA of the user based on the specified optical power.

BRIEF DESCRIPTION OF DRAWINGS

These and/or other aspects will become apparent and more readily appreciated from the following description of the example embodiments, taken in conjunction with the accompanying drawings in which.

DETAILED DESCRIPTION

Figure 1:
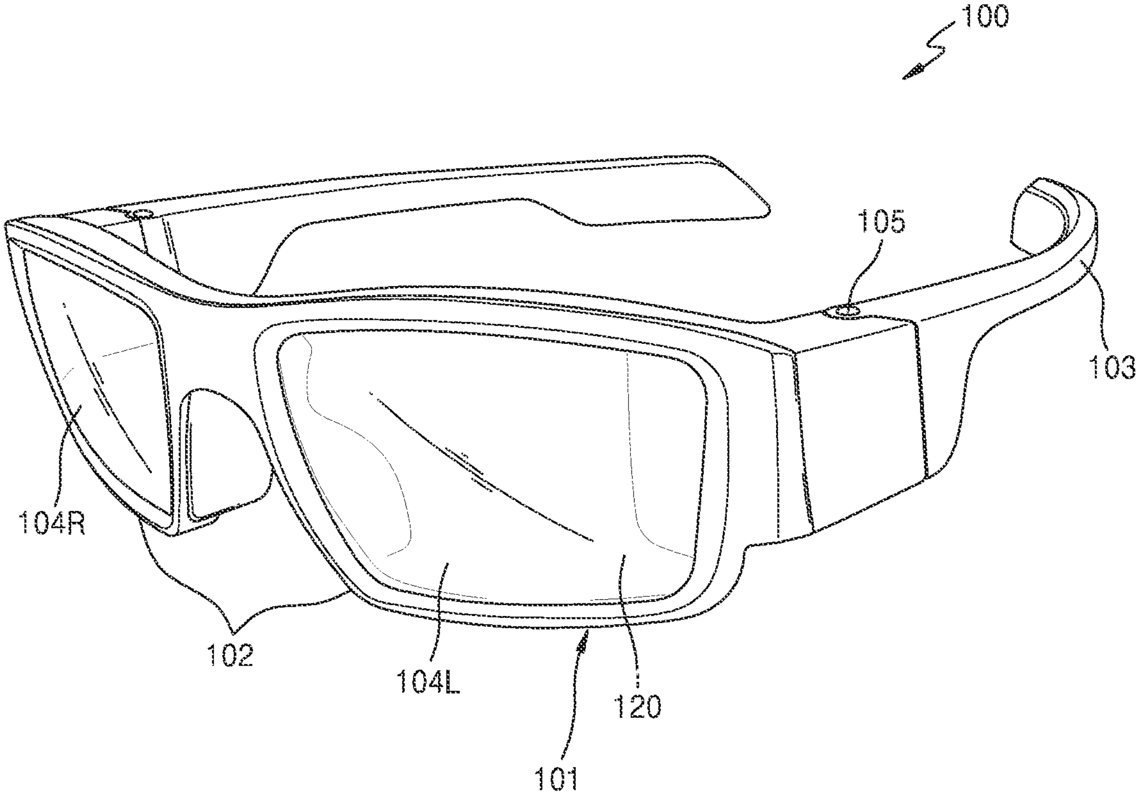
FIG. 1 is a diagram showing an exterior of an apparatus according to an embodiment of the disclosure.

Throughout the disclosure, the expression “at least one of a, b or c” indicates only a, only b, only c, both a and b, both a and c, both b and c, all of a, b, and c, or variations thereof.

Hereinafter, embodiments of the disclosure will be described in detail with reference to the attached drawings to allow those of ordinary skill in the art to easily carry out the embodiments of the disclosure. However, the disclosure may be implemented in various different forms, and are not limited to the embodiments of the disclosure described herein. To clearly describe the disclosure, parts that are not associated with the description have been omitted from the drawings, and throughout the specification, identical reference numerals refer to identical parts, and the size of each component may be exaggerated for clarity and convenience of description.

Although terms used in embodiments of the disclosure are selected with general terms popularly used at present under the consideration of functions in the disclosure, the terms may vary according to the intention of those of ordinary skill in the art, judicial precedents, or introduction of new technology. In addition, in a specific case, the applicant voluntarily may select terms, and in this case, the meaning of the terms may be disclosed in a corresponding description part of an embodiment of the disclosure. Thus, the terms used in herein should be defined not by the simple names of the terms but by the meaning of the terms and the contents throughout the disclosure.

Singular forms include plural forms unless apparently indicated otherwise contextually. When a portion is referred to as “comprises” a component, the portion may not exclude another component but may further include another component unless stated otherwise.

In the disclosure, visual acuity (VA) may refer to the spatial resolving ability of eyes, i.e., the ability of the eyes to identify fine details when a stationary object is seen with the eyes. Excessively high or low ametropia is a cause for myopia or hyperopia, which may be corrected with a means such as glasses, contact lenses, vision correction surgery, or the like. Corrected VA may be measured VA of a user wearing a lens having a certain optical power. User’s VA may be represented by an optical power of a lens required for corrected VA. For example, when a user has corrected VA with a spherical concave lens of about −1.00 D, the user may have myopia VA of about −1.00 D.

In the disclosure, an optical power may refer to a power for changing a direction of a light ray or an optical path by a curved surface or diffractive pattern of a lens, and may be understood as a term corresponding to a refractive power in a typical refractive lens. The unit of the optical power may be $m^{-1}$ or diopter (D), a value of which is expressed with a reciprocal number of a focal distance. The diopter is referred to as a power of a lens having a corresponding optical power. A sign of the optical power is positive (+) when a light ray converges as in a convex lens, and the sign of the optical power may be negative (−) when the light ray diverges as in a concave lens.

A spherical lens power may refer to an optical power of a spherical lens or a lens corresponding to the spherical lens, and is circularly symmetrical with respect to a center of a sphere.

A cylindrical lens power may refer to an optical power of a cylindrical lens or a lens corresponding to the cylindrical lens, and is bisymmetrical about a cylinder axis or an axis corresponding thereto. The cylindrical lens power may express an axial direction together with a diopter. For example, 1.00 D CYL at 90° means a cylindrical lens with a cylindrical axis inclined at 90° counterclockwise with respect to a horizontal reference line and an optical power of 1.00 D.

Hereinafter, the disclosure will be described in detail with reference to the accompanying drawings.

Figure 2:
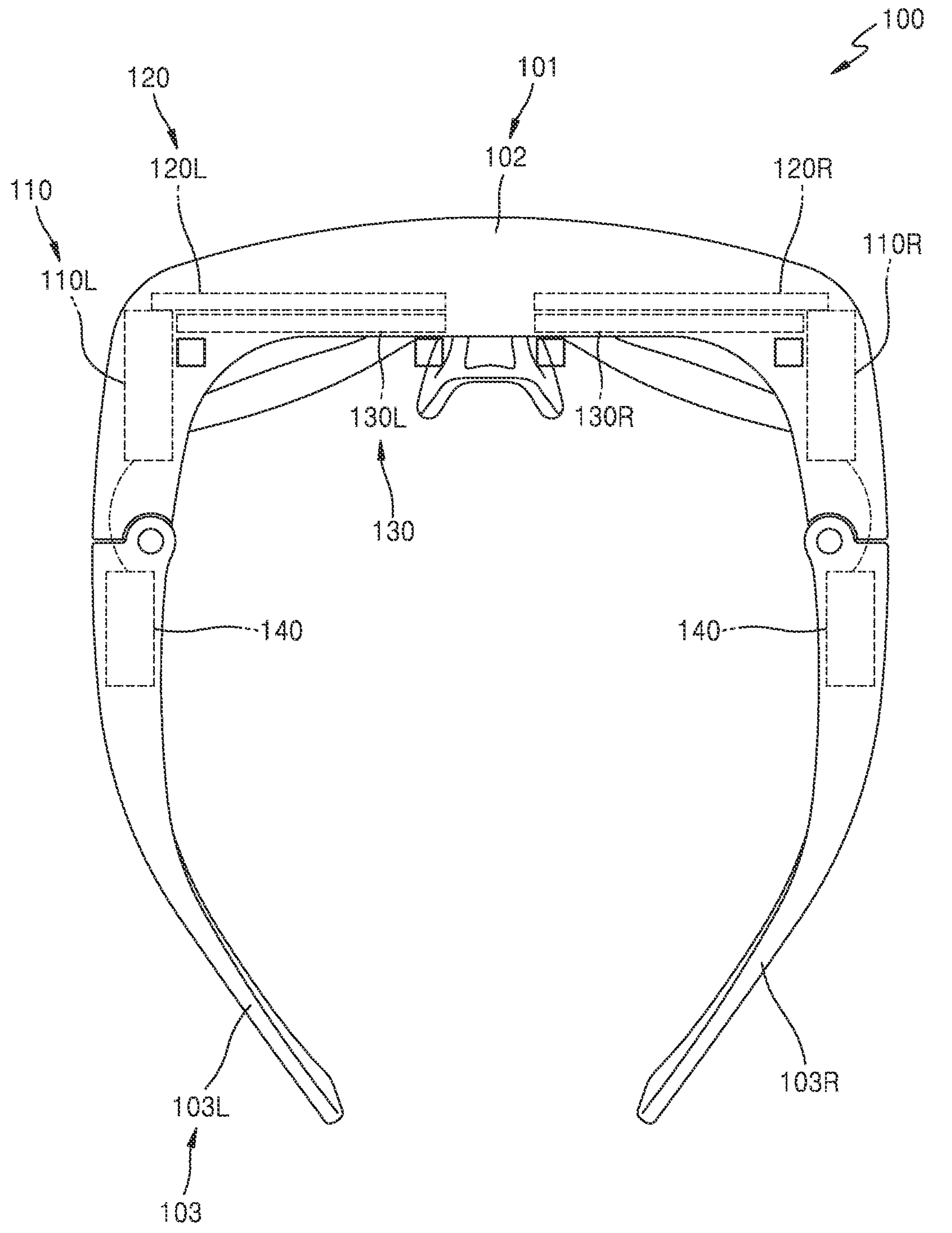
FIG. 2 is a plan view of an apparatus according to an embodiment of the disclosure.

FIG. 1 shows an exterior of an apparatus 100 according to an embodiment of the disclosure, and FIG. 2 is a plane view of the apparatus 100 according to an embodiment of the disclosure.

Referring to FIGS. 1 and 2, the apparatus 100 according to the current embodiment of the disclosure, which is AR glasses configured to be wearable on the user, may be an optical system showing both a virtual image and a real scene.

The apparatus 100 according to the embodiment of the disclosure may include a glass-type body 101. The glass-type body 101 may include, for example, a frame 102 and temples 103. The frame 102 in which a left glass lens 104L and a right glass lens 104R are positioned may have, for example, the shape of two rims connected by a bridge. The left and right glass lenses 104L and 104R are examples, and may have or may not have an optical power (a power). According to another embodiment, the left and right glass lenses 104L and 104R may be integrally formed, and in this case, the rims of the frame 102 may not be distinguished from the bridge. The left and right glass lenses 104L and 104R may be omitted.

The temples 103 may be respectively connected to both ends of the frame 102 and extend in a direction. The frame 102 and the temples 103 may be connected by a hinge 105. The hinge 105 is an example, such that a known member connecting the frame 102 to the temples 103 may be used. In another example, the frame 102 and the temples 103 may be integrally (or continuously) connected.

In the glass-type body 101, a display engine 110, an image combiner 120, a focus-tunable lens 130, and electronic parts 140 may be arranged.

The display engine 110 may be configured to project light of a virtual image. In an embodiment of the disclosure, the display engine 110 may include a left display engine 110L and a right display engine 110R. For example, the left display engine 110L and the right display engine 110R may be positioned at both end portions of the frame 102. In another example, the left display engine 110L and the right display engine 110R may be respectively positioned at a left temple 103L and a right temple 103R. In an embodiment of the disclosure, the display engine 110 may be installed in any one of the left display engine 110L and the right display engine 110R.

In an embodiment of the disclosure, the display engine 110 may include an illuminating optical system that illuminates light, an image panel that forms a two-dimensional virtual image by using the light illuminated from the illuminating optical system, and a projecting optical system that projects light of the virtual image formed in the image panel, and may have such a function as a subminiature projector. A light source of the illuminating optical system may be implemented, for example, with a light-emitting diode (LED) or a laser diode (LD). The image panel may be, for example, a liquid crystal panel, a liquid crystal on silicon (LCoS) panel, or a digital micromirror device (DMD) panel. The projecting optical system may include a projection lens of at least one element.

In an embodiment of the disclosure, the display engine 110 may include an illuminating optical system that illuminates light and a two-axis scanner that two-dimensionally scans the illuminated light.

In an embodiment of the disclosure, the display engine 110 may include an illuminating optical system that illuminates light, a linear image panel (i.e., a 1-dimensional image) using the light illuminated from the illuminating optical system, and a 1-axis scanner that scans light of the linear image formed in the linear image panel.

The image combiner 120 may guide the light output from the display engine 110 and light of a real scene to a target region, and may be, but not limited to, a waveguide, multiple mirrors, or a reflective mirror (including a flat mirror, a free-form surface mirror, etc.). The target region may be an eye motion box of the user.

In an embodiment of the disclosure, the image combiner 120 may include a left image combiner 120L and a right image combiner 120R. For example, the left image combiner 120L and the right image combiner 120R may be respectively arranged on a left side of the frame 120 and a right side of the frame 120. The left image combiner 120L and the right image combiner 120R may be arranged on or attached to the left glass lens 104L and the right glass lens 104R, respectively. The left image combiner 120L and the right image combiner 120R may be respectively at positions of the left glass lens 104L and the right glass lens 104R, and the left glass lens 104L and the right glass lens 104R may be omitted. The left image combiner 120L and the right image combiner 120R may be mounted on the frame 102 separately from the left glass lens 104L and the right glass lens 104R. In another example, the left image combiner 120L and the right image combiner 120R may be integrally configured and mounted on the frame 120. In another example, any one of the left image combiner 120L and the right image combiner 120R may be arranged on the glass-type body 101.

Figure 3:
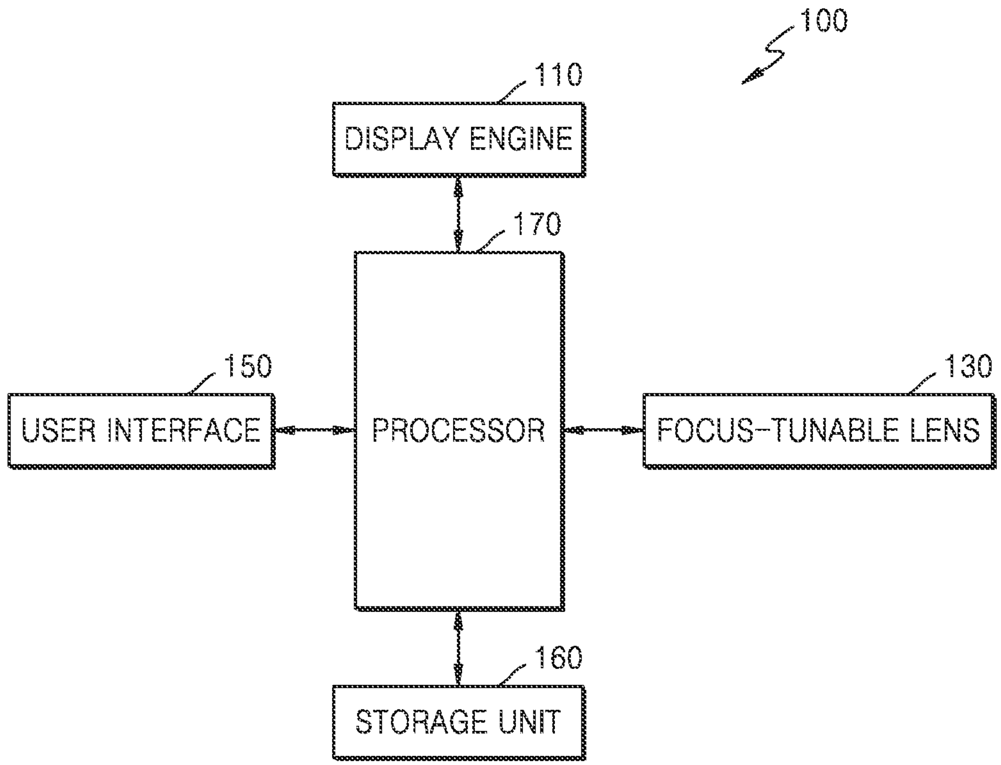
FIG. 3 is a block diagram of an apparatus according to an embodiment of the disclosure.

The focus-tunable lens 130 is a lens with a focal distance controllable by an electrical control signal of a processor 170 (of FIG. 3). The focus-tunable lens 130 may be arranged on a path of the light projected by the display engine 110. In an embodiment of the disclosure, the focus-tunable lens 130 may be arranged between the image combiner 120 and a target region (in other words, an eye motion box). In an embodiment of the disclosure, the focus-tunable lens 130 may be arranged such that an effective lens region covers an output region of the image combiner 120. The effective lens region refers to a region where an optical power is assigned on a lens surface of the focus-tunable lens 130. The effective lens region of the focus-tunable lens 130 may include a plurality of different lens regions to which different optical powers are assigned by a control signal of the processor 170.

The focus-tunable lens 130 may include an electroactive material layer and an addressable electrode array configured to assign different voltage profiles to a plurality of different regions of the electroactive material layer. An electroactive material of the electroactive material layer may be formed such that a refractive index changes with a voltage applied to an electrode array. The electroactive material may be any one of nematic liquid crystal, smectic liquid crystal, or cholesteric liquid crystal, polymer gel, electro-active polymer (EAP), liquid crystal polymer, polymer dispersed liquid crystal (PDLC), polymer stabilized liquid crystal (PSLC), and a self-assembled nonlinear supramolecular structure. The electroactive material may be appropriately selected based on requirements of a focus-tunable lens, such as a response time, a magnitude of a driving voltage, and a liquid crystal alignment control method. The electrode array may be, for example, a stripe electrode, a pixel array, etc., and may be appropriately selected according to requirements of the focus-tunable lens, such as an optical power, etc.

The electronic parts 140 may include a user input interface (user input device) 150, a storage 160, and a processor 170, as shown in a block diagram of FIG. 3. The electronic parts 140 may be positioned in any one of the frame 102 or the temples 103 of the glass-type body 101 or may be in a plurality of positions in a distributed manner, or may be mounted on a printed circuit board (PCB) substrate, a flexible PCB (FPCB) substrate, etc. A lens driver circuit for driving the focus-tunable lens 130 may be arranged adjacent to the focus-tunable lens 130. In another example, the entire lens driver circuit or a part thereof may be positioned, for example, on a main board.

FIG. 3 is a block diagram of the apparatus 100 according to an embodiment of the disclosure. Among components shown in FIG. 3, a component having the same reference numeral as that of a component shown in FIG. 2 is the same as the component shown in FIG. 2. Thus, a redundant description will be omitted.

The user input interface 150 may receive a user input from the user to control the apparatus 100. In an embodiment of the disclosure, the user input interface 150 may include, but not limited to, at least any one of a gaze tracking sensor, a microphone, a button, a touch pad, or a gesture recognition sensor. In an embodiment of the disclosure, the user input interface 150 may receive, as a user input, a gaze direction of the user, tracked by the gaze tracking sensor. In an embodiment of the disclosure, the user input interface 150 may receive, as a user input, a user's voice input through the microphone. In an embodiment of the disclosure, the user input interface 150 may receive, as a user input, pressing of a button or a touch on a touch pad (a capacitive overlay scheme, a resistive overlay scheme, an infrared beam scheme, a surface acoustic wave scheme, an integral strain gauge scheme, a piezoelectric scheme, etc.) by the user. In an embodiment of the disclosure, the user input interface 150 may receive, as a user input, a user's gesture detected by a camera or a gesture recognition sensor like a proximity sensor. The user input interface 150 may include various input devices such as a key pad, a dome switch, a touch pad, a jog wheel, a jog switch, etc. The user input interface 150 may receive a user response in a process of measuring VA of the user.

The storage 160 may store various commands or data, programs, or applications for driving and controlling the apparatus 100 and input/output signals or data of a virtual image, under the control of the processor 170. The programs stored in the storage 160 may be classified into a plurality of modules, e.g., a VA measuring module, a VA correcting module, etc., depending on functions thereof. As examples of various data driving and controlling the apparatus 100, an optical power variable range, a VA measuring image, etc., of the focus-tunable lens 130 may be stored in advance in the storage 160. A voltage profile for operating the focus-tunable lens 130 with a corresponding refractive power may be stored in advance.

The storage 160 may include at least one type of hardware devices among, for example, flash memory type, random access memory (RAM), static random access memory (SRAM), read-only memory (ROM), electrically erasable programmable ROM (EEPROM), programmable ROM (PROM), magnetic memory, a magnetic disc, and an optical disc.

The processor 170 may control the overall operation of the apparatus 100 including the display engine 110 and the focus-tunable lens 130 and perform various data processing and operations including image data, by driving an operating system or an application. For example, the processor 170 may load the VA measuring module from the storage 160, determine an optical power to be assigned to a different lens region of the focus-tunable lens 130 according to a process of the VA measuring module, and control the focus-tunable lens 130 by a control signal corresponding to the optical power. For example, the control signal may be a voltage profile applied to the focus-tunable lens 130. In another example, the control signal may be a control command signal corresponding to preset voltage profiles. When the user views a virtual image or a real scene, the processor 170 may determine the optical power of the focus-tunable lens 130 based on VA information of the user and control the focus-tunable lens 130 by a control signal corresponding to the determined optical power.

The processor 170 may include, for example, at least one hardware among a central processing unit (CPU), a microprocessor, a graphic processing unit (GPU), application specific integrated circuits (ASICs), digital signal processors (DSPs), digital signal processing devices (DSPDs), programmable logic devices (PLDs), or field programmable gate arrays (FPGAs), without being limited thereto.

Figure 4:
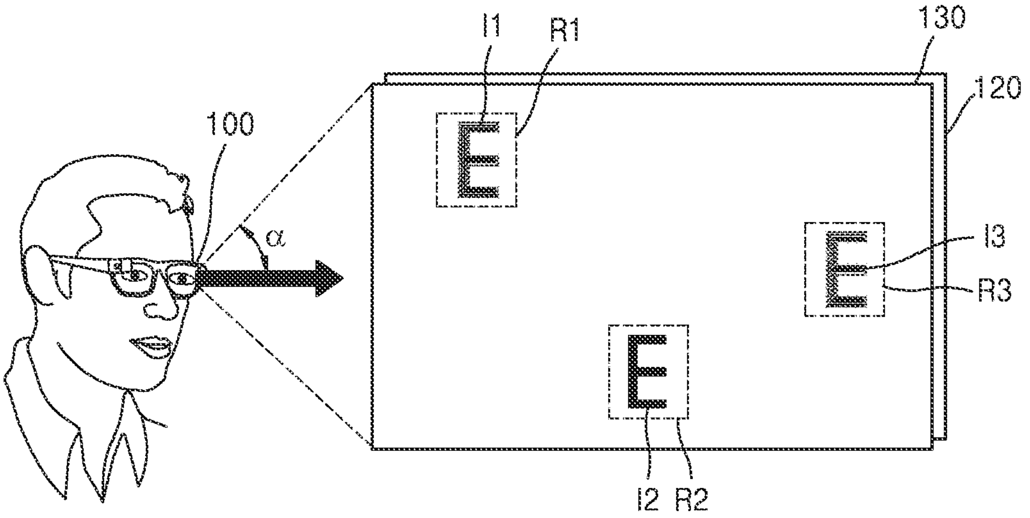
FIG. 4 is a diagram showing an example of measuring a visual acuity (VA) of a user by using an apparatus according to an embodiment of the disclosure.
Figure 5:
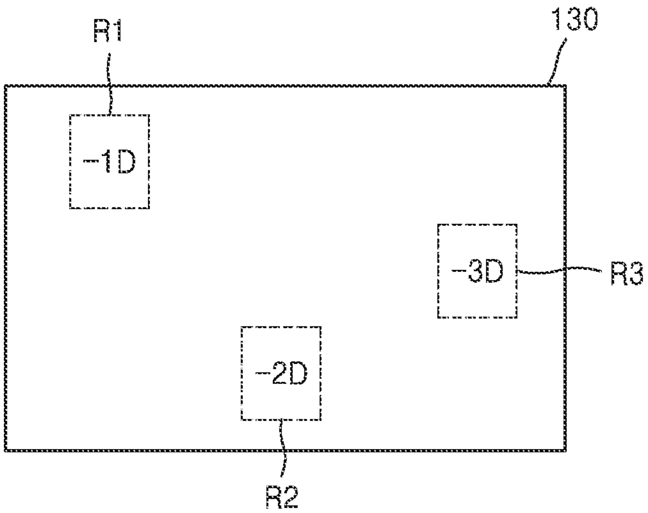
FIG. 5 is a diagram showing an example of an optical power of a focus-tunable lens according to an embodiment of the disclosure.

FIG. 4 is a diagram showing an example where the apparatus 100 according to an embodiment of the disclosure measures VA of a user (a wearer), and FIG. 5 is a diagram showing an example of an optical power of the focus-tunable lens 130 according to an embodiment of the disclosure.

Referring to FIGS. 4 and 5, the user may view a first VA measuring image I1, a second VA measuring image I2, and a third VA measuring image I3 which are output through an output region of the image combiner 120 and pass through the user 130.

The effective lens region of the focus-tunable lens 130 may have a size configured to simultaneously display the first to third VA measuring images I1, I2, and I3. For example, a minimum size S of the effective lens region of the focus-tunable lens 130 may satisfy Equation 1 provided below.

$$S=S_0+2r\tan\alpha \qquad \text{[Equation 1]}$$

Herein, $S_0$ indicates a size of a pupil, r indicates an eye relief distance, and a indicates a gaze angle with respect to the first to third VA measuring images I1, I2, and I3.

The processor 170 may control the focus-tunable lens 130 to assign different optical powers to the first lens region R1, the second lens region R2, and the third lens region R3. For example, as shown in FIG. 5, the first to third lens regions R1, R2, and R3 of the focus-tunable lens 130 may be controlled to have optical powers of about +1.00 diopter (D), about +2.00 D, and about +3.00 D, respectively. The first to third lens regions R1, R2, and R3 of the focus-tunable lens 130 may be separated from one another such that the user may view them at a time and compare them on one screen.

The first to third VA measuring images I1, I2, and I3 output from the display engine 110 and guided in the image combiner 120 may be transmitted to a user's retina after passing through the first to third lens regions R1, R2, and R3 of the focus-tunable lens 130. Thus, the first to third VA measuring images I1, I2, and I3 having passed through the first to third lens regions R1, R2, and R3 may be transmitted to the user's retina at a time, in a state of being refracted at different degrees by the optical powers applied to the first to third lens regions R1, R2, and R3.

The first to third VA measuring images I1, I2, and I3 may be, for example, but not limited to, a character or a figure. The first to third VA measuring images I1, I2, and I3 may be, for example, but not limited to, a character or a figure.

The light of the virtual image projected from the display engine 110 and output through the image combiner 120 may be regarded as a substantially parallel beam of light. For example, the light of the virtual image output through the image combiner 120 may be regarded as light substantially emitted from an infinite focus. Herein, substantially may indicate that the virtual image is sufficiently far, substantially close to an infinite focus (e.g., at a distance of about 5 m) in terms of visual perspective recognized by a human.

A user having normal VA may clearly see a VA measuring image at a sufficient distance close to an infinite focus (e.g., a distance of about 5 m). For example, when the focus-tunable lens 130 does not assign optical powers to the first to third lens regions R1, R2, and R3, the user having normal VA may see a clear VA measuring image. However, as shown in FIG. 5, when an optical power of + diopter is assigned to the first to third lens regions R1, R2, and R3 of the focus-tunable lens 130, the first to third VA measuring images I1, I2, and I3 having passed through the first to third lens regions R1, R2, and R3 may be refracted such that the user having normal VA may not clearly see the first to third VA measuring images I1, I2, and I3.

When the user has ametropia, the user needs a correcting lens to see a clear image due to the ametropia. When the user has myopia VA of about −2.00 D (that is, the user needs a correcting lens of about −2.00 D), the user may most clearly see the second VA measuring image I2 having passed through the second lens region R2 assigned with an optical power of about −2.00 D, as shown in FIGS. 4 and 5. However, the user having myopia VA of about −2.00 D may see a blurred first VA measuring image I1 having passed through the first lens region R1 assigned with an optical power of about −1.00 D, and see less clearly the third VA measuring image I3 having passed through the third lens region R3 assigned with an optical power of about −3.00 D because the third VA measuring image I3 is reduced excessively small.

Thus, the processor 170 may cause the first to third VA measuring images I1, I2, and I3 to be output to first to third output regions of the image combiner 120 corresponding to the first to third lens regions R1, R2, and R3 while controlling the focus-tunable lens 130 to assign different optical powers to the first to third lens regions R1, R2, and R3 of the focus-tunable lens 130, inquire the user about which image is clearly visible to the user, receive a user response thereto, and determine user's VA.

In an embodiment of the disclosure, an operation of inquiring the user about which image is clearly visible to the user may be performed by the processor 170 controlling the display engine 110 to display on a screen, a text (e.g., "select the most clearly visible image", "watch the most clearly visible image", "point your finger at the most clearly visible image", "select one image or a plurality of images visible clearly", etc.) or may be guided by voice through a speaker.

An input operation for the user's response may be performed through the user input interface 150.

In an embodiment of the disclosure, the user input interface 150 may include a microphone, and the user may response by voice, for example, "I see the middle image most clearly". In this case, the processor 170 may specify the second lens region R2 through which the middle image (i.e., the second VA measuring image I2) passes.

In an embodiment of the disclosure, the user input interface 150 may include a gaze tracking sensor, and the user may watch a specific image (e.g., the second VA measuring image I2) for several seconds. In this case, the processor 170 may specify the second lens region R2 where a user's gaze tracked by the gaze tracking sensor stays longer than a reference time (e.g., 2 seconds).

In an embodiment of the disclosure, the user input interface 150 may include a gesture recognition sensor, and the user may point a specific image (e.g., the second VA measuring image I2) with a finger in a space seen through the apparatus 100. In this case, the processor 170 may specify the second lens region R2 pointed by the finger of the user recognized through the gesture recognition sensor.

An input scheme of the user input interface 150 is not limited to the above examples, and the user's input may be possible with various input schemes such as a touch pad, a jog wheel, etc.

The processor 170 may determine the user's VA based on a region specified by the user's input. For example, when an image that is most clearly visible to the user is the second VA measuring image I2, the processor 170 may determine that an optical power of about −2.00 D assigned to the second lens region R2 through which the second VA measuring image I2 passes corrects user's ametropia. Thus, when a region specified by a user's input is the second lens region R2, the processor 170 may determine the optical power of about −2.00 D assigned to the second lens region R2 as a correcting optical power (in other words, user's VA).

In this way, as the user compares the first to third VA measuring images I1, I2, and I3 seen on one screen at a time and select the most clearly visible image, VA measurement is performed. Such an inquiry and response process may be repeated a plurality of times while adjusting the optical powers assigned to the first to third lens regions R1, R2, and R3 of the focus-tunable lens 130, thereby more accurately determining user's VA.

While the embodiment of the disclosure describes a case where different optical powers are assigned to three lens regions (i.e., the first to third lens regions R1, R2, and R3) of the focus-tunable lens 130, embodiments are not limited thereto. For example, different optical powers may be assigned to two different lens regions or four or more different lens regions of the focus-tunable lens 130.

Figure 6:
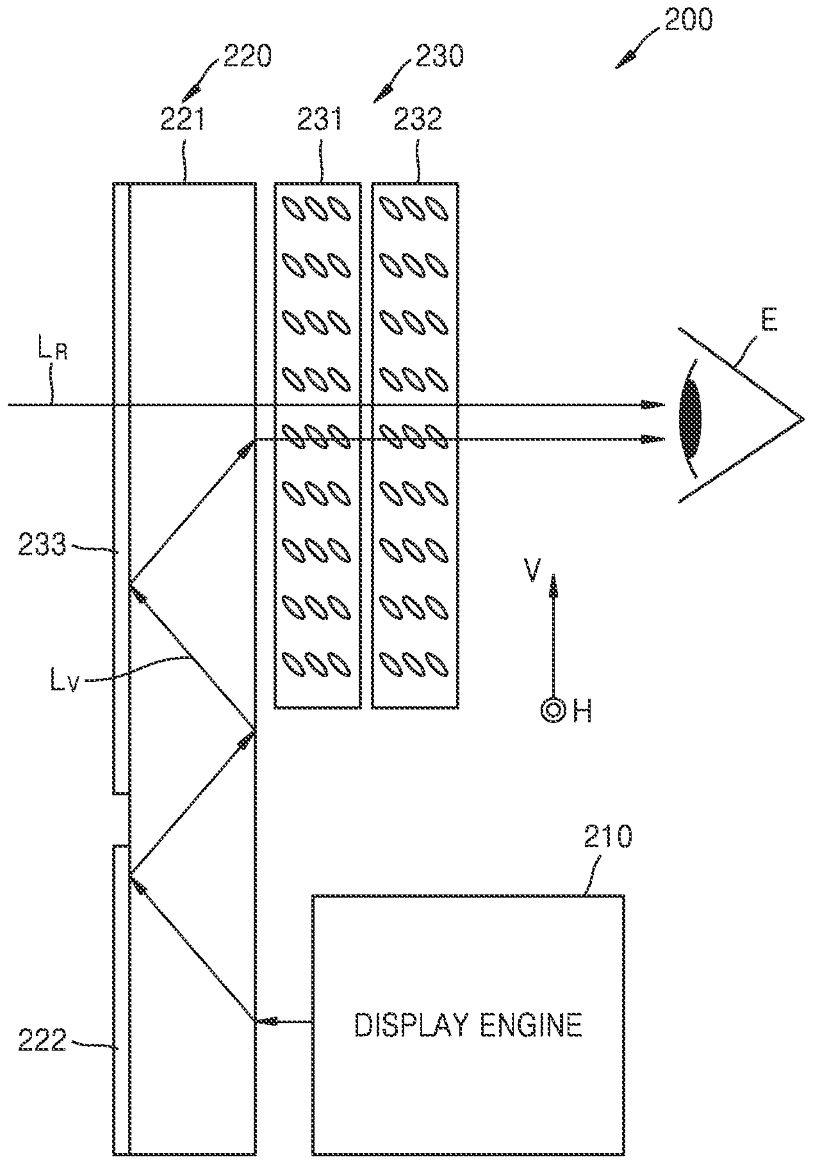
FIG. 6 is a diagram showing optical arrangement of an apparatus according to an embodiment of the disclosure.

FIG. 6 is a diagram showing optical arrangement of an apparatus 200 according to an embodiment of the disclosure.

Referring to FIG. 6, the apparatus 200 according to an embodiment of the disclosure, which is an AR optical system configured to show both a virtual image and a real scene, may include a display engine 210, an image combiner 220, and a focus-tunable lens 230.

The display engine 210 may be configured to project the light $L_V$ of the virtual image. The display engine 210 may be substantially the same as the display engine 110 in the above-described embodiment of the disclosure, and thus will not be described redundantly.

The image combiner 220 may include a waveguide 221 that guides light by internal total reflection. The waveguide 221 may be formed as a single layer or multiple layers of a transparent material in which the light may propagate while being internally reflected. Herein, the transparent material may refer to a material through which light in a visible light band passes, and a transparency thereof may not be 100% and the transparent material may have a certain color. The waveguide 221 may have the shape of a flat plate or a curved plate. As the waveguide 221 is formed of a transparent material, light $L_R$ of a real scene may pass through the waveguide 221. Thus, when the user wears the apparatus 100, the user may see not only a virtual image, but also the real scene, through the apparatus 100 such that the apparatus 100 may implement augmented reality (AR).

The waveguide 221 may include an input region to which light $L_V$ of the virtual image projected from the display engine 110 is input and an output region from which the light $L_V$ of the incident virtual image is output to a target region. The target region may be an eye motion box of the user. The input region and the output region are separated from each other. The image combiner 220 may include an input coupler 222 and an output coupler 223 that are provided in the input region and the output region of the waveguide 221, respectively. The input coupler 222 may be formed on at least one of a surface of the waveguide 221, which faces or opposes the display engine 110, or an inside of the waveguide 221. Similarly, the output coupler 223 may be formed on at least one of a surface of the waveguide 221, which faces or opposes the target region (the eye motion box), or an inside of the waveguide 221. The input coupler 222 and the output coupler 223 may be a diffractive element or a meta element. Examples of the diffractive element may include, but not limited to, a diffractive optical element (DOE), a holographic optical element (HOE), a volume holographic optical element (VHOE), and a surface relief grating (SRG). The meta element has a meta surface structured in a pattern in which incident light is smaller than a wavelength band (i.e., of a surf wavelength), for example, may be, but not limited to, a meta grating or a meta lens having a pattern in which the incident light is smaller than the wavelength band.

Between the input region and the output region of the waveguide 221, a propagation region may be provided. In the propagation region of the waveguide 221, a propagation element may be provided through which the light $L_V$ of the virtual image input from the input region propagates. The propagation element may be the diffractive element or the meta element. The propagation element may be positioned between the input region and the output region or may be positioned overlappingly with at least a part of the input region or the output region. The propagation element may be integrally formed with the output coupler 223. The propagation element may be an expansion grating that causes the light $L_V$ of the input virtual image be replicated into multiple ones. The expansion grating may be adapted to split the light $L_V$ of the virtual image into a plurality of beamlets for propagation across the entire output region, when the light $L_V$ propagates through total reflection in the waveguide 221. The output coupler 223 may be adapted to output the light $L_V$ propagating in the waveguide 221 to the outside of the waveguide 221 and may also perform a role of the propagation element (e.g., the expansion grating).

The light $L_V$ of the virtual image output through the output coupler 223 may be substantially regarded as a parallel beam. In an embodiment of the disclosure, the projecting optical system of the display engine 110 may include a collimating lens, and the light $L_V$ of the virtual image emitted by the collimating lens may be parallel light, such that the light $L_V$ of the virtual image finally delivered to the eyes through the waveguide 221 may be substantially regarded as a parallel beam.

The focus-tunable lens 230 may include a first strip electrode liquid crystal lens 231 and a second strip electrode liquid crystal lens 232. The first and second strip electrode liquid crystal lenses 231 and 232 may be arranged between the image combiner 220 and the target region. The first and second strip electrode liquid crystal lenses 231 and 232 may be driven to simulate cylindrical lenses, respectively. The first and second strip electrode liquid crystal lenses 231 and 232 may be overlappingly arranged such that axial directions thereof are orthogonal to each other. For example, the first strip electrode liquid crystal lens 231 may simulate a cylindrical lens with a vertical direction V as a cylindrical axis, and the second strip electrode liquid crystal lens 232 may simulate a cylindrical lens with a horizontal direction H as a cylindrical axis. The first strip electrode liquid crystal lens 231 may simulate a cylindrical lens with the horizontal direction H as a cylindrical axis, and the second strip electrode liquid crystal lens 232 may simulate a cylindrical lens with the vertical direction V as a cylindrical axis.

Figure 7:
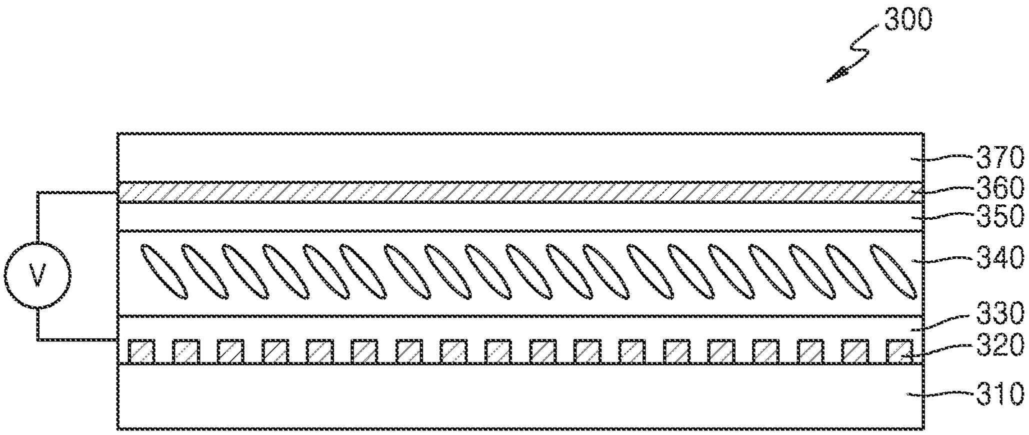
FIG. 7 shows a first strip electrode liquid crystal lens according to an embodiment of the disclosure.
Figure 8:
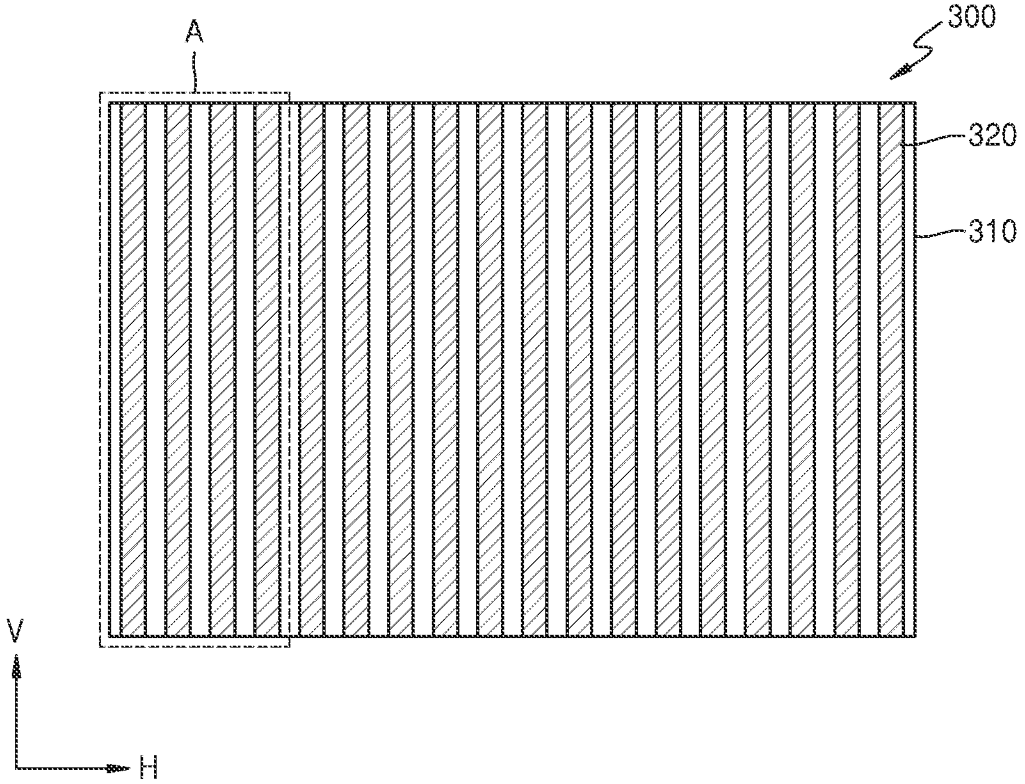
FIG. 8 shows a strip electrode array of a first strip electrode liquid crystal lens according to an embodiment of the disclosure.

FIG. 7 shows a first strip electrode liquid crystal lens 300 according to an embodiment of the disclosure, and FIG. 8 shows a strip electrode array of the first strip electrode liquid crystal lens 300 according to an embodiment of the disclosure.

Referring to FIGS. 7 and 8, the first strip electrode liquid crystal lens 300 may be structured such that a liquid crystal layer 340 is between a first substrate 310 and a second substrate 370. A plurality of first strip electrodes 320 may be provided on the first substrate 310. Each first strip electrode 320 may be a transparent electrode having a longitudinal shape extending long in the vertical direction V. The plurality of first strip electrodes 320 may be arranged in parallel in the horizontal direction H. Widths of the respective first strip electrodes 320 may be, but not limited to, the same as one another. Voltage may be applied to the first strip electrodes 320 individually (or independently) or in the unit of a certain group. A common second electrode (common electrode) 360 may be provided on the second substrate 370. The second electrode 360 may be, but not limited to, a flat-type transparent electrode serving as a reference electrode for the first strip electrodes 320. The positions of the first strip electrodes 320 and the second electrode 360 may be interchanged with each other. Reference numerals 330 and 350 may indicate alignment layers that align liquid crystal molecules in the liquid crystal layer 340 in a certain direction. The original alignment of the liquid crystal molecules may be determined by a direction of a force applied from the alignment layers 330 and 350, but upon application of proper voltage, the liquid crystal molecules may rotate. Thus, when voltage is applied to the liquid crystal layer 340, the refractive index of the liquid crystal layer 340 may change due to realignment of the liquid crystal molecules. As the refractive index of the liquid crystal layer 340 is spatially adjusted by applying a voltage profile to the first strip electrodes 320, the liquid crystal layer 340 may provide a phase profile having a desired optical power.

Figure 9:
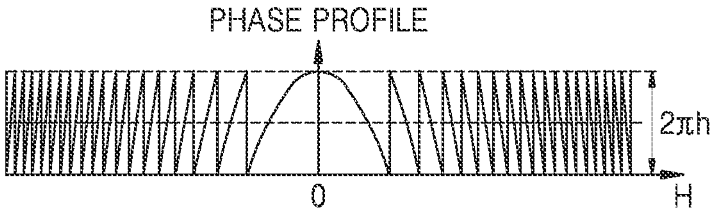
FIG. 9 shows a phase profile of a first strip electrode liquid crystal lens that simulates a cylindrical lens.

FIG. 9 shows a phase profile of the first strip electrode liquid crystal lens 300 that simulates a cylindrical lens. The phase profile shown in FIG. 9 indicates a phase difference of light waves passing through one lens region A of the first strip lens liquid crystal lens 300 with respect to coordinates in the horizontal direction H, in which the lens region A may be understood as a Fresnel zone corresponding to a cylindrical lens. As described above, the refractive index of the liquid crystal layer 340 may change with voltage applied to the first strip electrodes 320, such that by applying an appropriate voltage profile to the first strip electrodes 320 passing through the lens region A, a refractive index distribution in the lens region A may simulate the Fresnel zone corresponding to the cylindrical lens. The first strip lens liquid crystal lens 300 may simulate a convex cylindrical lens having a positive (+) optical power or a concave cylindrical lens having a negative (−) optical power, according to the voltage profile applied to the first strip electrodes 320.

Figure 10:
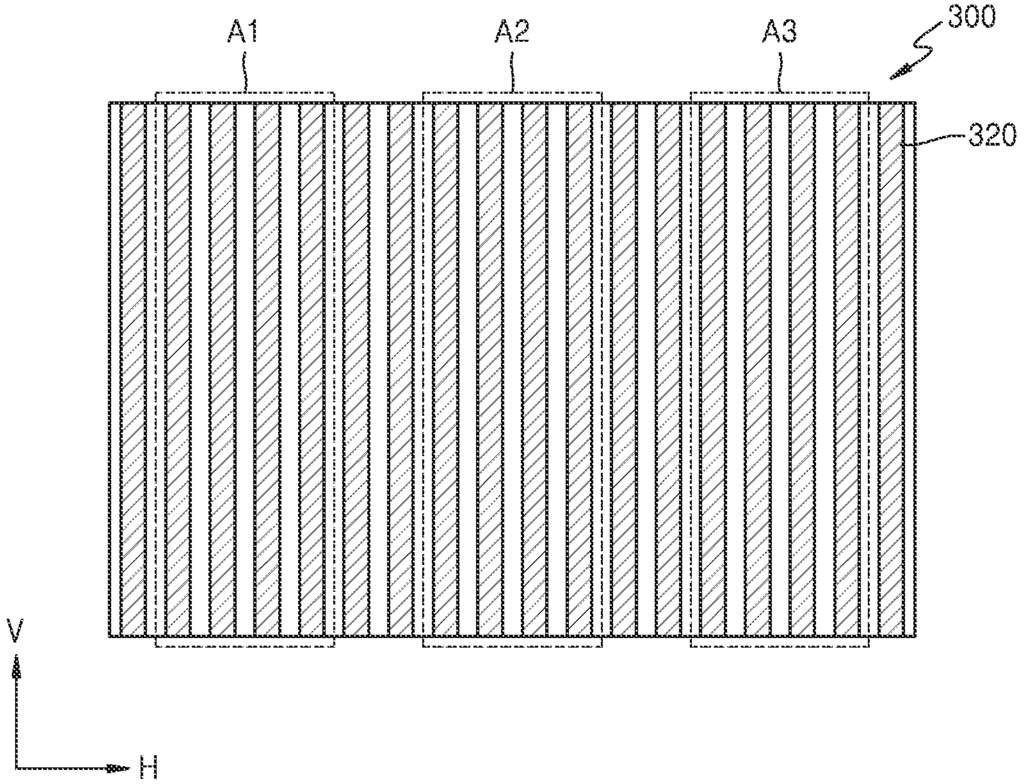
FIG. 10 shows an example where a first strip electrode liquid crystal lens is divided into three lens regions, according to an embodiment of the disclosure.

FIG. 10 shows an example where the first strip electrode liquid crystal lens 300 is divided into three lens zones A1, A2, and A3, according to an embodiment of the disclosure. The three zones A1, A2, and A3 are obtained by dividing an aperture of the first strip lens liquid crystal lens 300 in the horizontal direction H. For example, the first strip electrodes 320 having a longitudinal shape extending long in the vertical direction V may be grouped into the three zones A1, A2, and A3. By applying a certain voltage profile to the first strip electrodes 320 for each of the three zones A1, A2, and A3, the three zones A1, A2, and A3 may be adapted to respectively simulate cylindrical lenses having optical powers, e.g., of about +1 D, about +2 D, and about +3 D with the vertical direction V as axes thereof.

Figure 11:
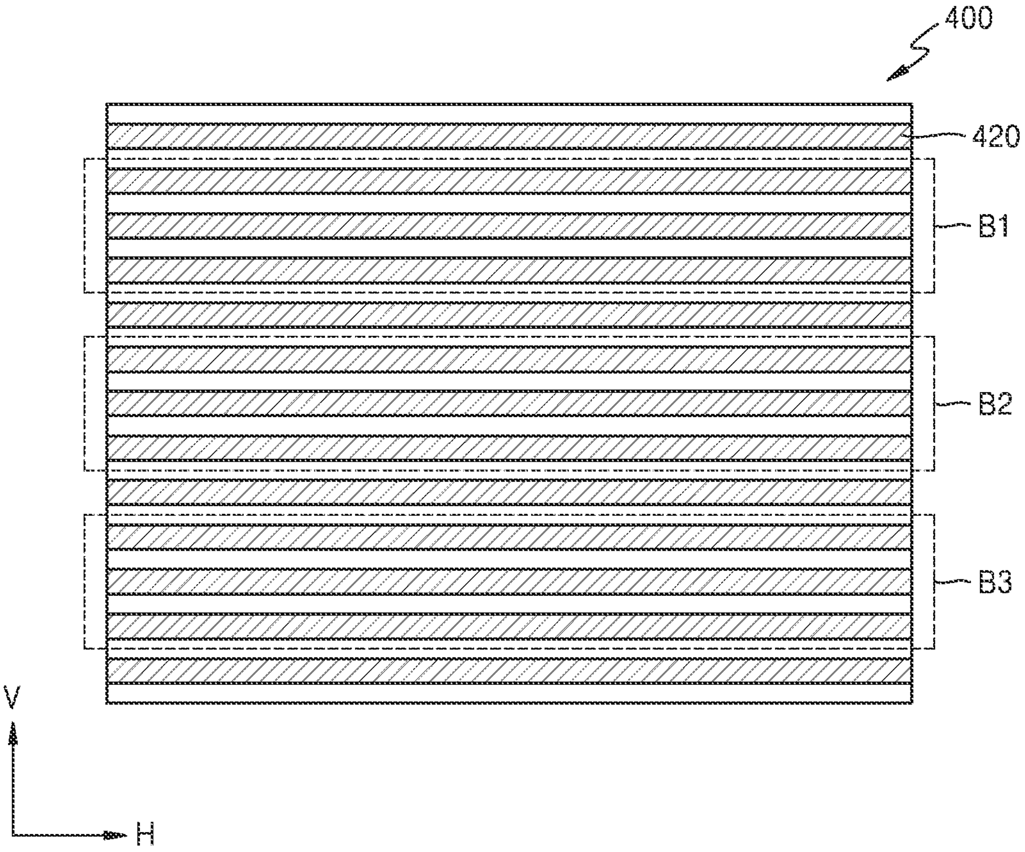
FIG. 11 shows an example where a second strip electrode liquid crystal lens is divided into three lens regions, according to an embodiment of the disclosure.

FIG. 11 shows an example where the second strip electrode liquid crystal lens 400 is divided into three lens zones B1, B2, and B3, according to an embodiment of the disclosure. An aperture of the second strip electrode liquid crystal lens 400 may also be divided into the three zones B1, B2, and B3 in the vertical direction V. As an appropriate voltage profile is applied to the second strip electrodes 420, the three zones B1, B2, and B3 of the second strip electrode liquid crystal lens 400 may be adapted to simulate cylindrical lenses having optical powers, e.g., of about +1 D, about +3 D, and about +2 D with the horizontal direction H as axes thereof.

Figure 12:
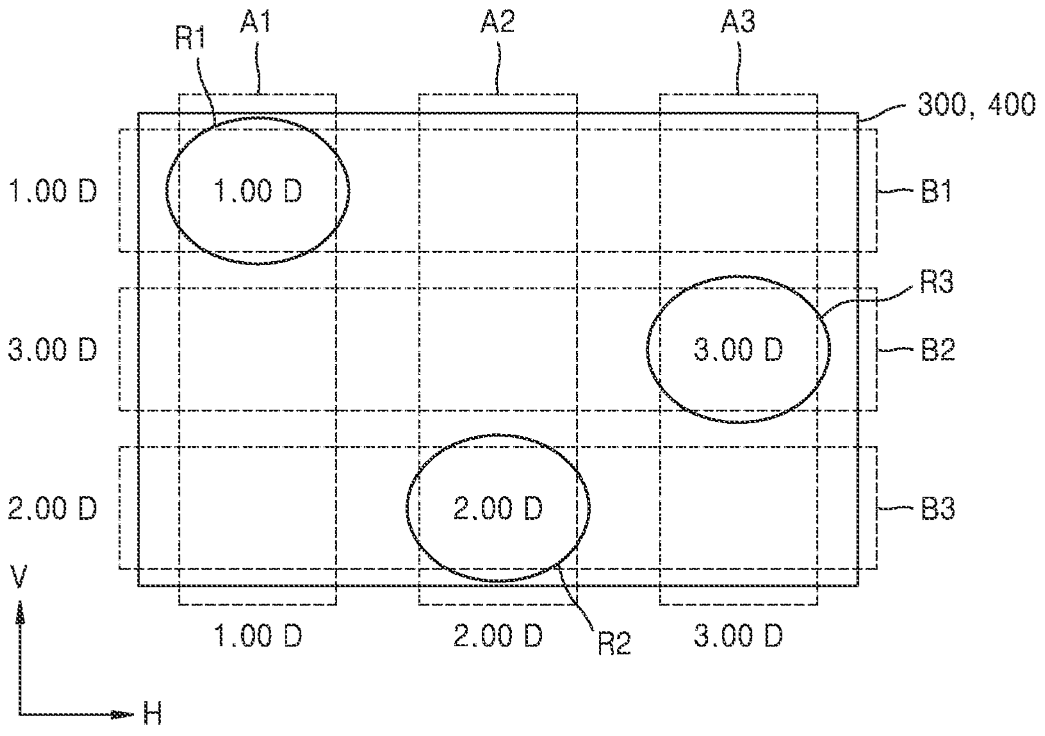
FIG. 12 shows an example of optical powers assigned to different lens regions by first and second strip electrode liquid crystal lenses according to an embodiment of the disclosure.

FIG. 12 shows an example of optical powers assigned to different lens regions by the first and second strip electrode liquid crystal lenses 300 and 400 according to an embodiment of the disclosure. Referring to FIG. 12, an axis of the first strip electrode liquid crystal lens 300 is placed in the vertical direction V, an axis of the second strip electrode liquid crystal lens 400 is placed in the horizontal direction H, and the first strip electrode liquid crystal lens 300 and the second strip electrode liquid crystal lens 400 are arranged to overlap, i.e., overlay each other, such that the optical power of the first strip electrode liquid crystal lens 300 and the optical power of the second strip electrode liquid crystal lens 400 may be added to each other. In this case, a magnitude of the optical power of the first strip electrode liquid crystal lens 300, with an axis in the vertical direction V, and a magnitude of the optical power of the second strip electrode liquid crystal lens 400, with an axis in the horizontal direction H, are equal to each other, such that the summed optical power may be regarded as substantially a spherical lens power. For example, the first lens region R1 may have a spherical lens power of about +1.00 D as a sum of a cylindrical lens power of about +1.00 D of the first strip lens liquid crystal lens 300 in the vertical direction V and a cylindrical lens power of about +1.00 D of the second strip lens liquid crystal lens 400 in the horizontal direction H. In addition, the second and third lens regions R2 and R3 may have spherical lens powers of about +2.00 D and about +3.00 D, respectively. A spherical lens power assigned to the first to third lens regions R1, R2, and R3 may change with a voltage profile applied to the three zones A1, A2, and A3 of the first strip electrode liquid crystal lens 300 and the three zones B1, B2, and B3 of the second strip electrode liquid crystal lens 400. When the spherical lens power assigned to the first to third lens regions R1, R2, and R3 is positive (+), the spherical lens power may be used to measure hyperopia, and when the spherical lens power assigned to the first to third lens regions R1, R2, and R3 is negative (−), the spherical lens power may be used to measure myopia.

Figure 13:
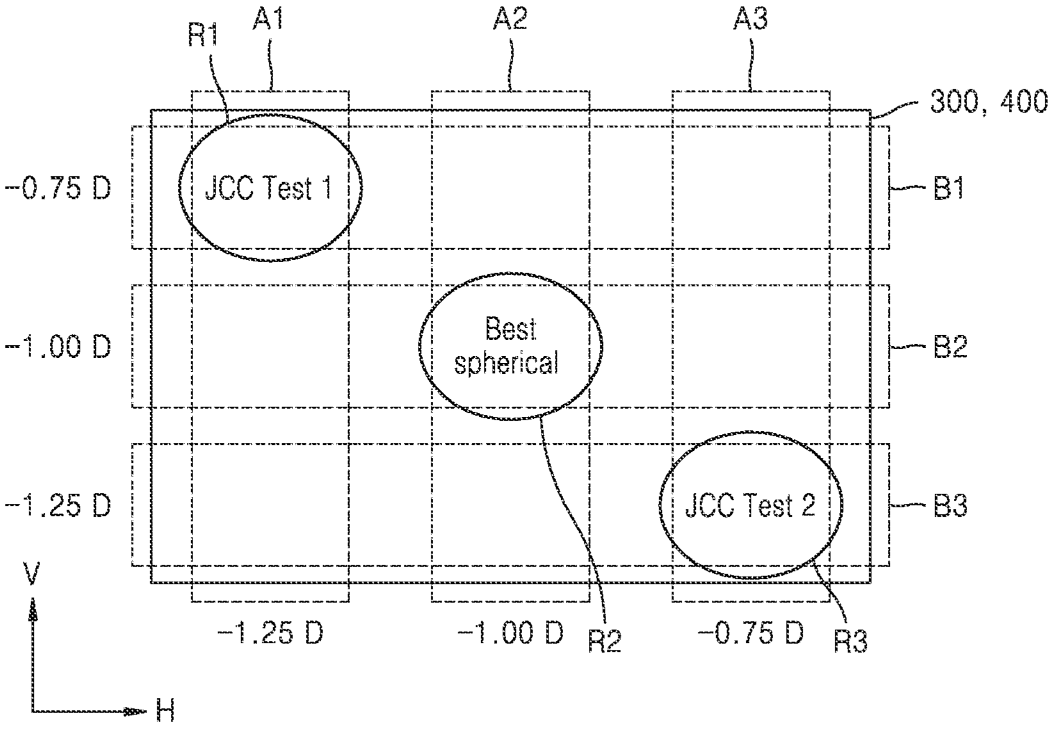
FIG. 13 shows an example of optical powers assigned to different lens regions in first and second strip electrode liquid crystal lenses according to an embodiment of the disclosure.

FIG. 13 shows an example of optical powers assigned to different lens regions by the first and second strip electrode liquid crystal lenses 300 and 400 according to an embodiment of the disclosure. Referring to FIG. 13, the magnitude of the optical power of the first strip liquid crystal lens 300 with an axis in the vertical direction V and the magnitude of the optical power of the second strip liquid crystal lens 400 with an axis in the horizontal direction H may be different from each other, in some of the first to third lens regions R1, R2, and R3. For example, the first lens region R1 may cause the magnitude of the optical power of the first strip electrode liquid crystal lens 300 with the axis in the vertical direction V to be greater than the magnitude of the optical power of the second strip electrode liquid crystal lens 400 with the axis in the horizontal direction H, and the third lens region R3 may cause the magnitude of the optical power of the first strip electrode liquid crystal lens 300 with the axis in the vertical direction V to be less than the magnitude of the optical power of the second strip electrode liquid crystal lens 400 with the axis in the horizontal direction H. As a result, the first lens region R1 and the third lens region R3 may have orthogonal spherical lens powers, together with spherical lens powers of the same magnitude. The second lens region R2 may cause the magnitude of the optical power of the first strip electrode liquid crystal lens 300, with the axis in the vertical direction V, and the magnitude of the optical power of the second strip electrode liquid crystal lens 400, with the axis in the horizontal direction H, to be equal to each other, thus having a spherical lens power.

For example, the three zones A1, A2, and A3 of the first strip electrode liquid crystal lens 300 may simulate cylindrical lenses having optical powers, e.g., of about −1.25 D, −1.00 D, and −0.75 D, respectively, with axes in the vertical direction V, and the three zones B1, B2, and B3 of the second strip electrode liquid crystal lens 400 may simulate cylindrical lenses having optical powers, e.g., of about −0.075 D, about −1.00 D, and about −1.25 D, respectively, with axes in the horizontal direction H. Thus, the first lens region R1 may have the cylindrical lens power of about −1.25 D in the vertical direction V through the first strip lens liquid crystal lens 300 and the cylindrical lens power of about −0.75 D in the horizontal direction H through the second strip electrode liquid crystal lens 400, thus having a spherical lens power of about −0.75 D and a cylindrical lens power of about −0.50 D in the vertical direction V (briefly, expressed as −0.75 D SPH/−0.50 D CYL at 90°). The second lens region R2 may have a spherical lens power of about −1.00 D and a cylindrical lens power of about 0.00 D (i.e., −1.00 D SPH), and the third lens region R3 may have a spherical lens power of about −0.75 D and a cylindrical lens power of about −0.50 D in the horizontal direction H (i.e., −0.75 D SPH/−0.50 D CYL at 180°). An optical power assigned to the first to third lens regions R1, R2, and R3 may change with a voltage profile applied to the three zones A1, A2, and A3 of the first strip electrode liquid crystal lens 300 and the three zones B1, B2, and B3 of the second strip electrode liquid crystal lens 400. Such different cylindrical lens powers of the first lens region R1 and the third lens region R3 may respectively correspond to a reverse direction reversed from a forward direction of a cross cylindrical lens (e.g., Jackson cross cylinder (JCC)) used in a related subjective refraction test, and may be used to measure astigmatism of the user. An existing JCC test method searches for an axial direction that is most clearly visible to the user while sequentially changing the cylinder axis in the forward direction and the reverse direction, and the embodiment of the disclosure allows the user to select an axial direction while seeing different axial directions at the same time.

Figure 14:
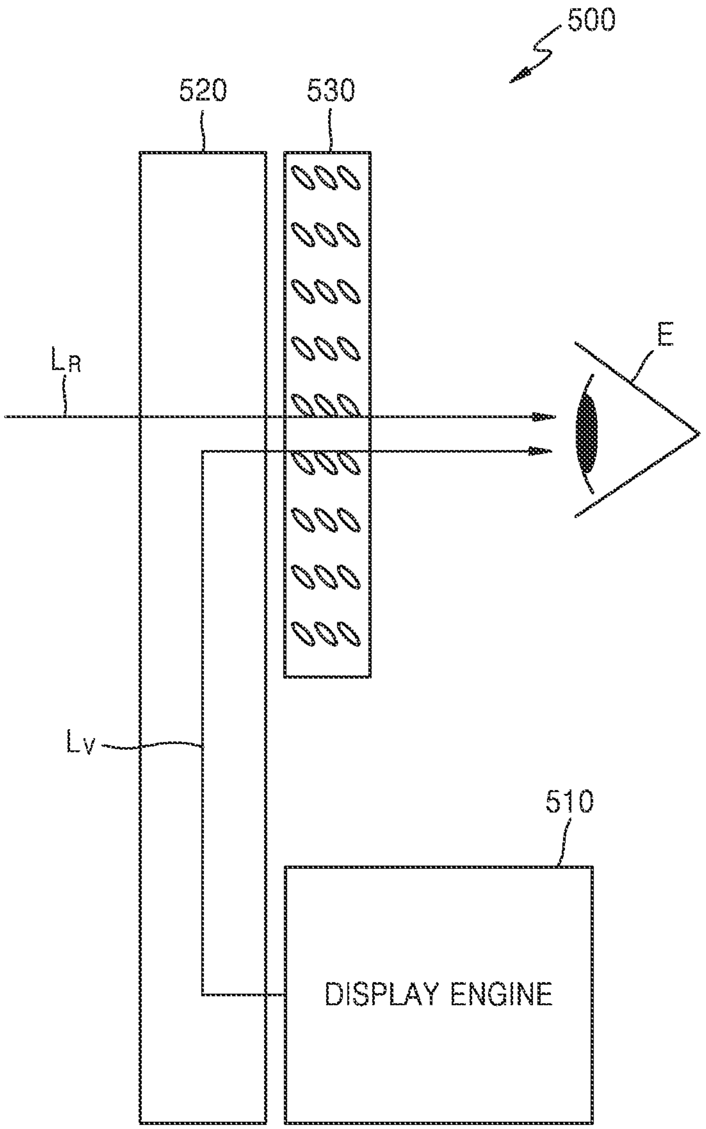
FIG. 14 is a diagram showing optical arrangement of an apparatus according to an embodiment of the disclosure.

FIG. 14 is a diagram showing optical arrangement of an apparatus according to an embodiment of the disclosure.

Referring to FIG. 14, an apparatus 500 according to an embodiment of the disclosure may be an AR optical system including a display engine 510, an image combiner 520, and a focus-tunable lens 530. The display engine 510 and the image combiner 520 may be substantially the same as the display engines 110 and 210 and the image combiners 120 and 220 of the optical systems 100 and 200 described with reference to FIG. 6, and thus will not be described redundantly.

The focus-tunable lens 530 may be a single pixel electrode liquid crystal lens. The focus-tunable lens 530 may be arranged between the image combiner 520 and the target region.

Figure 15:
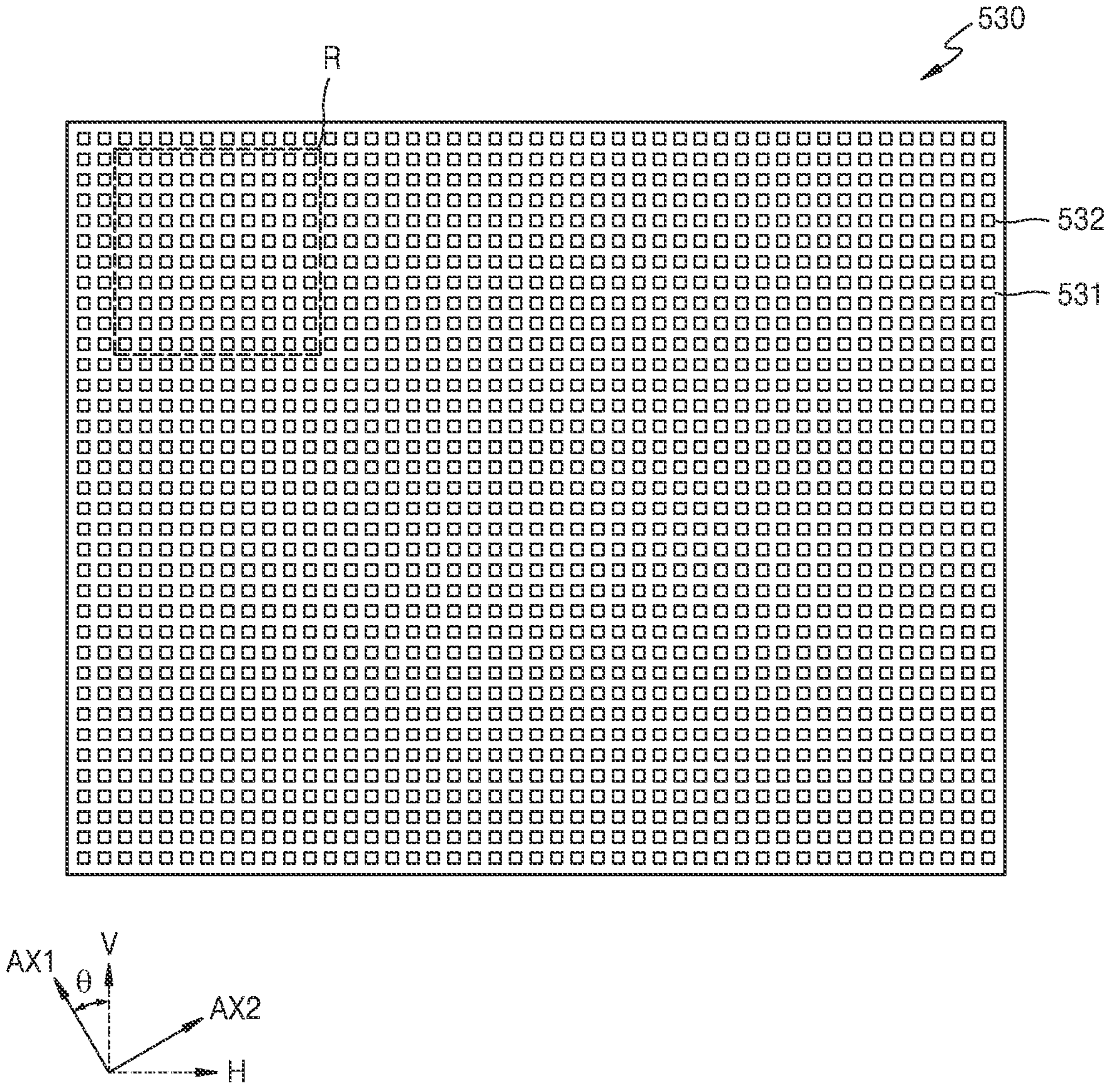
FIG. 15 shows a pixel electrode array of a focus-tunable lens according to an embodiment of the disclosure.

FIG. 15 shows a pixel electrode array of the focus-tunable lens 530 according to an embodiment of the disclosure. Referring to FIG. 15, the focus-tunable lens 530 may be structured such that a liquid crystal layer is between two opposing substrates. On a substrate 531, a plurality of pixel electrodes 532 may be arranged two-dimensionally. Each of the pixel electrodes 532 may have a rectangular shape, without being limited thereto. Voltage may be applied to the pixel electrodes 532 individually (or independently) or in the unit of a certain group. A common second electrode (a common electrode) may be provided on the other substrate opposing the substrate 531. A liquid crystal layer, two substrates, and a second electrode (a common electrode) are substantially the same as the liquid crystal layer 340, the first and second substrates 310 and 370, and the second electrode 360 described with reference to FIG. 7, and thus will not be described redundantly.

Figure 16:
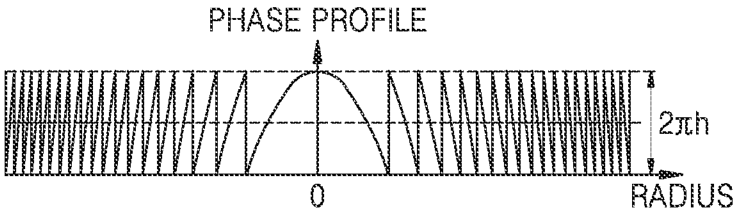
FIG. 16 shows a phase profile of a focus-tunable lens in a case where a lens region of a focus-tunable lens simulates a convex lens.

FIG. 16 shows a phase profile of the focus-tunable lens 530 in a case where a lens region R of the focus-tunable lens 530 simulates a convex lens. The phase profile shown in FIG. 16 indicates a phase difference of light waves passing through the focus-tunable lens 530 with respect to coordinates in a radial direction from the center of the lens region R, in which the lens region R may be understood as a Fresnel zone corresponding to a spherical lens. The lens region R of the focus-tunable lens 530 may simulate a convex spherical lens having a positive (+) optical power or a concave spherical lens having a negative (−) optical power, according to a voltage profile applied to the pixel electrodes 532 belonging to the lens region R.

By applying a voltage profile that is symmetric around a specific axis (the vertical direction V, the horizontal direction H, or an axis in a random direction) to the pixel electrodes 532 belonging to the lens region R, the lens region R may simulate a cylindrical lens with the axis as a cylinder axis. Voltage may be independently applied to each of the pixel electrodes 532, and an axial direction of the simulated cylindrical lens may not be limited to the vertical direction V or the horizontal direction H. For example, the lens region R may simulate a cylindrical lens with a first axis AX1 as the cylinder axis. In this case, a direction of the first axis AX1 may be a direction rotated counterclockwise by an angle 8 with respect to the vertical direction V. By applying an appropriate voltage profile to the pixel electrodes 532 belonging to the lens region R, the lens region R may simulate a lens having an optical power that is a sum of a certain spherical lens optical power and a certain cylindrical lens power. For example, the optical power assigned to the lens region R may be a sum of a cylindrical lens power with the first axis AX1 as a cylinder axis and a cylindrical lens power with the second axis AX3 as a cylinder axis. For example, the optical powers implemented by the first and second strip electrode liquid crystal lenses 300 and 400 may be implemented by the focus-tunable lens 530 that is a single pixel electrode liquid crystal lens.

Figure 17:
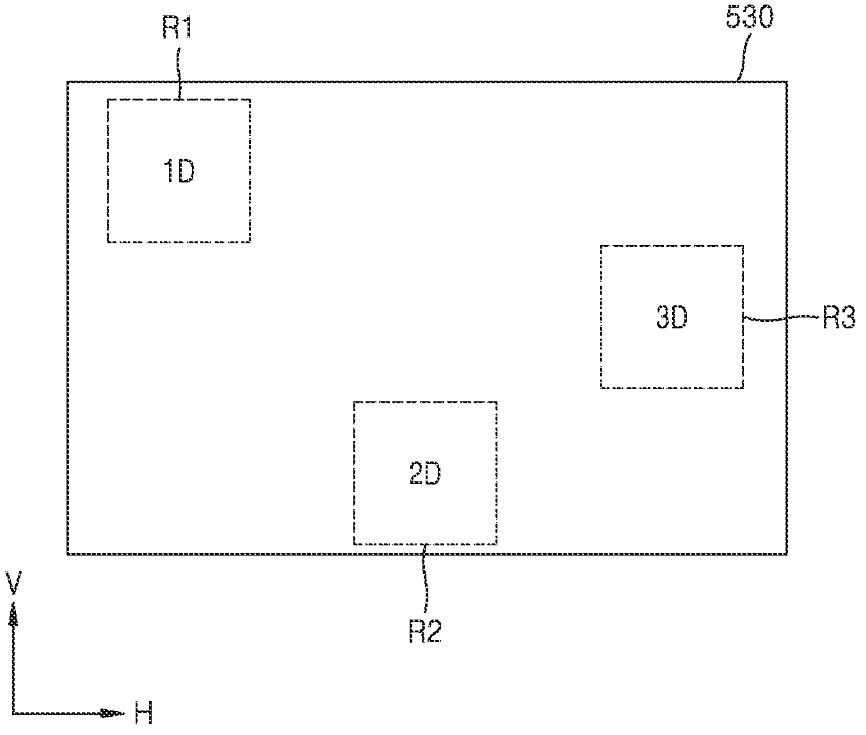
FIG. 17 shows an example of optical powers assigned to different lens regions in a focus-tunable lens according to an embodiment of the disclosure.

FIG. 17 shows an example of optical powers assigned to different lens regions in the focus-tunable lens 530, according to an embodiment of the disclosure. Referring to FIG. 17, as an appropriate voltage profile is applied to the pixel electrodes 532 belonging to the first lens region R1, the first lens region R1 may simulate a spherical lens having a spherical lens power of about +1 D. Similarly, as an appropriate voltage profile is applied to the pixel electrodes 532 belonging to the second lens region R2, the second lens region R2 may simulate a spherical lens having a spherical lens power of about +2 D, and as an appropriate voltage profile is applied to the pixel electrodes 532 belonging to the third lens region R3, the third lens region R3 may simulate a spherical lens having a spherical lens power of about +3 D. As such, when the optical power assigned to the first to third lens regions R1, R2, and R3 is positive (+), the spherical lens power may be used to measure hyperopia, and when the spherical lens power assigned to the first to third lens regions R1, R2, and R3 is negative (−), the optical power may be used to measure myopia.

Figure 18:
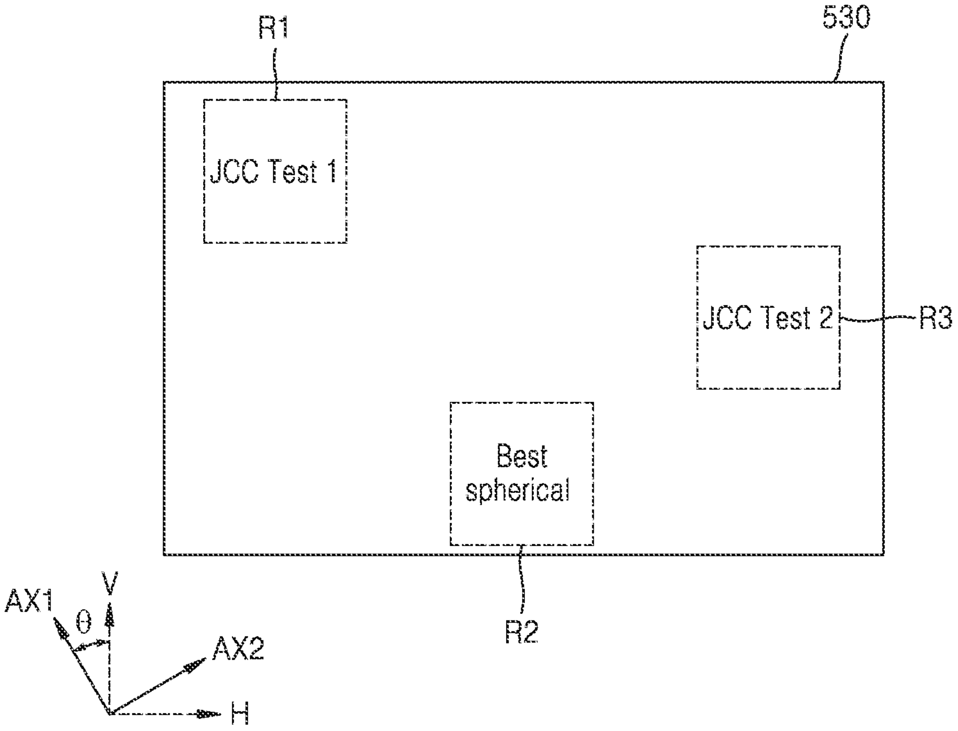
FIG. 18 shows an example of optical powers assigned to different lens regions in a focus-tunable lens according to an embodiment of the disclosure.

FIG. 18 shows an example of optical powers assigned to different lens regions in the focus-tunable lens 530, according to an embodiment of the disclosure. Referring to FIG. 18, as an appropriate voltage profile is applied to the pixel electrodes 532 belong to the first to third lens regions R1, R2, and R3 of the focus-tunable lens 530, the first to third lens regions R1, R2, and R3 may have cylindrical lens powers with different directions as axes. For example, the first lens region R1 may have a spherical lens power of about −0.75 D and a cylindrical lens power of about −0.50 D with a first direction AX1, the second lens region R2 may have a spherical lens power of about −1.00 D and a cylindrical lens power of about 0.00 D, and the third lens region R3 may have a spherical lens power of about −0.75 D and a cylindrical lens power of about −0.50 D with a second direction AX2.

Strengths or axial directions of optical powers assigned to the first to third lens regions R1, R2, and R3 may be finely changed with a voltage profile applied to the pixel electrodes 532 belonging to the first to third lens regions R1, R2, and R3, such that the apparatus 500 may be used for fine measurement of astigmatism.

In the apparatuses 100, 200, and 500 according to the foregoing embodiments of the disclosure, the image combiners 120, 220, and 520 may employ various well-known image combiners without being limited to a waveguide scheme.

Figure 19:
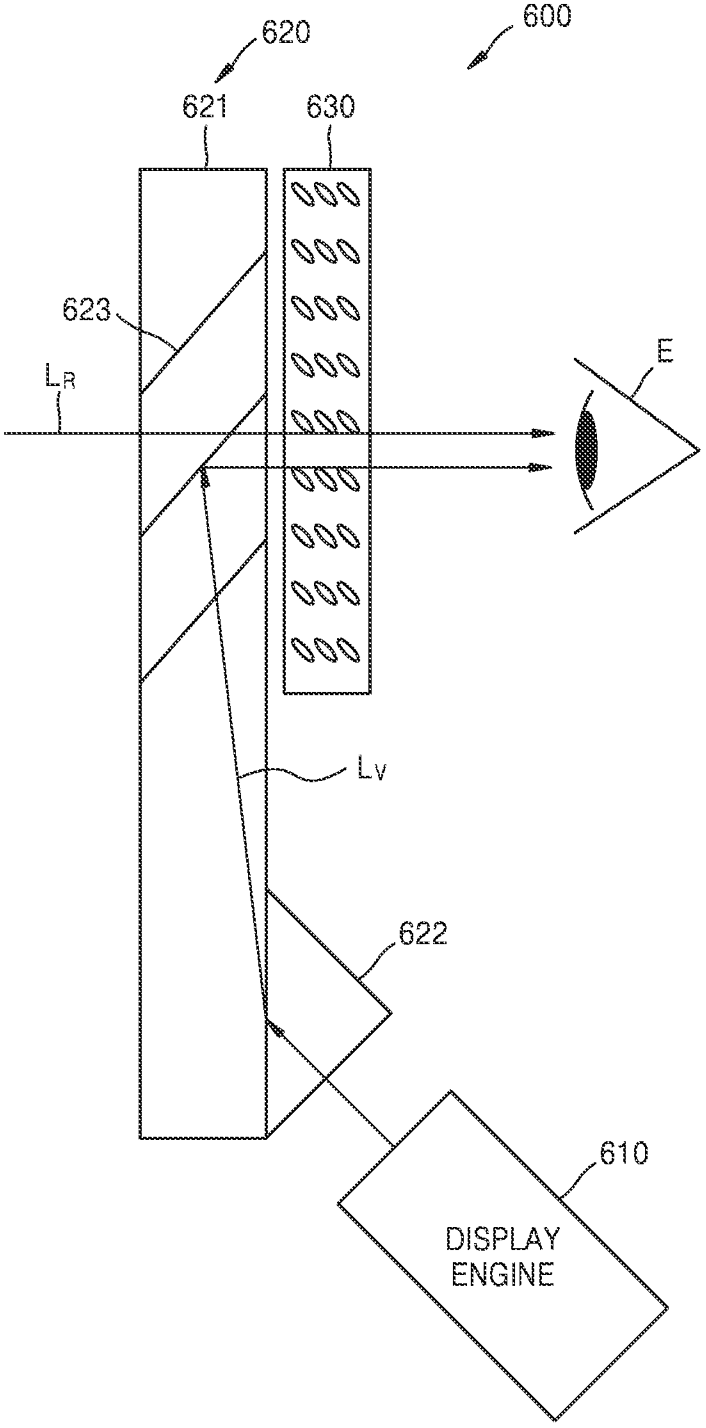
FIG. 19 is a diagram showing optical arrangement of an apparatus according to an embodiment of the disclosure.

FIG. 19 is a diagram showing optical arrangement of an apparatus 600 according to an embodiment of the disclosure. Referring to FIG. 19, an apparatus 600 according to an embodiment of the disclosure may be an AR optical system including a display engine 610, an image combiner 620, and a focus-tunable lens 630. The display engine 610 and the focus-tunable lens 630 may be substantially the same as the display engines 110, 210, and 510 and the focus-tunable lenses 130, 230, and 530 of the above-described apparatuses 100, 200, and 500, and thus will not be described redundantly. The image combiner 620 may include a transparent body 621, an input coupler 622 that inputs the light $L_V$ of the virtual image emitted from the display engine 610 to the transparent body 621, and an output coupler 623 that outputs the light $L_V$ of the virtual image input to the transparent body 621 to a target region (i.e., the eye motion box of the user). The input coupler 622 may include, for example, but not limited to, a prism. The output coupler 623 may include, for example, but not limited to, a plurality of micro-mirrors immersed in the transparent body 621. The output coupler 623 may reflect the light $L_V$ of the virtual image input to the transparent body 621 to the target region. The light $L_R$ of the real scene may pass through the transparent body 621 and be directed to the target region. When the output coupler 623 includes semi-transparent mirrors, the light $L_R$ of the real scene may pass through the output coupler 623 and be directed to the target region.

Figure 20:
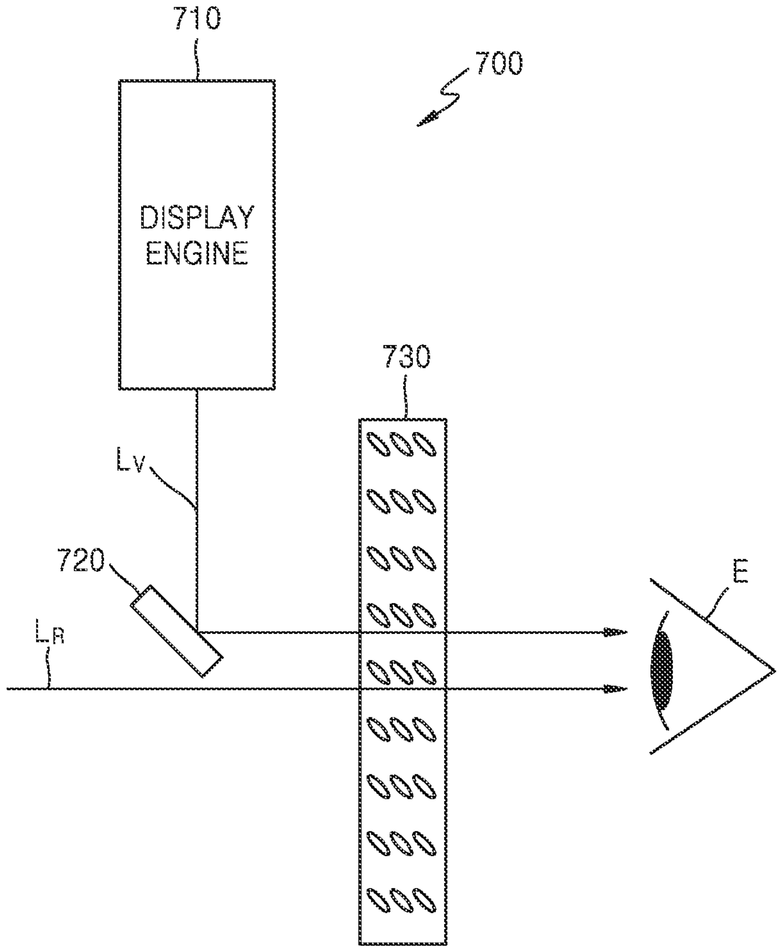
FIG. 20 is a diagram showing optical arrangement of an apparatus according to an embodiment of the disclosure.

FIG. 20 is a diagram showing optical arrangement of an apparatus 700 according to an embodiment of the disclosure. Referring to FIG. 20, the apparatus 700 according to an embodiment of the disclosure may be an AR optical system including a display engine 710, a reflective mirror 720, and a focus-tunable lens 730. The display engine 710 and the focus-tunable lens 730 may be substantially the same as the display engines 110, 210, and 510 and the focus-tunable lenses 130, 230, and 530 of the above-described apparatuses 100, 200, and 500, and thus will not be described redundantly. The reflective mirror 720 may reflect the light $L_V$ of the virtual image emitted from the display engine 710 to the target region (i.e., the user's eye motion box). The reflective mirror 720 may be a simple mirror, a curved mirror, a reflective prism, etc. The light $L_R$ of the real scene may be directed to the target region through an edge of the reflective mirror 720. When the reflective mirror 720 is a semi-transparent mirror, the light $L_R$ of the real scene may pass through the reflective mirror 720 and be directed to the target region.

Figure 21:
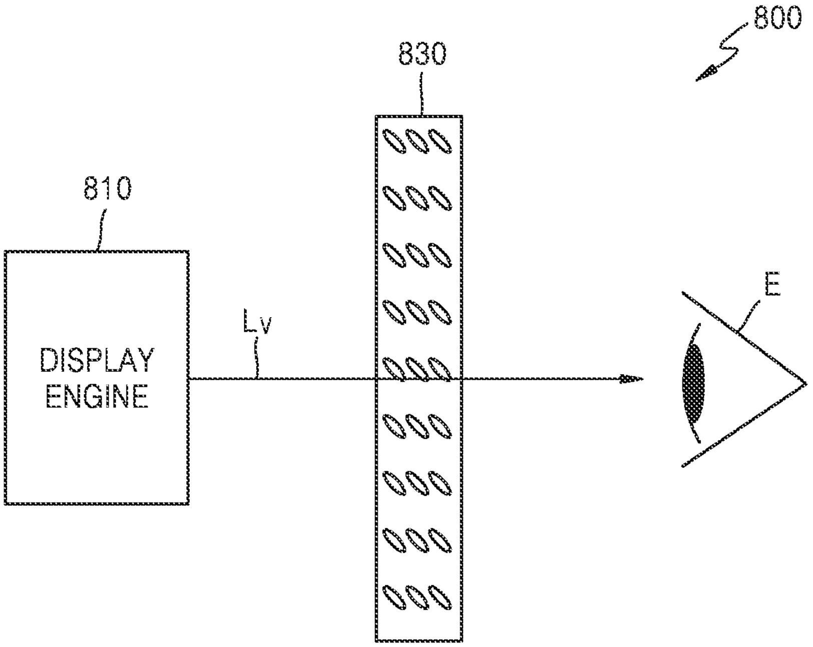
FIG. 21 is a diagram showing optical arrangement of an apparatus according to an embodiment of the disclosure.

FIG. 21 is a diagram showing optical arrangement of an apparatus 800 according to an embodiment of the disclosure. Referring to FIG. 21, the apparatus 800 according to an embodiment of the disclosure may be an AR optical system including a display engine 810 and a focus-tunable lens 830. A mechanical configuration of the display engine 810 and the focus-tunable lens 830 may be substantially the same as that of the display engines 110, 210, and 510 and the focus-tunable lenses 130, 230, and 530 of the above-described apparatuses 100, 200, and 500, and thus will not be described redundantly.

Figure 22:
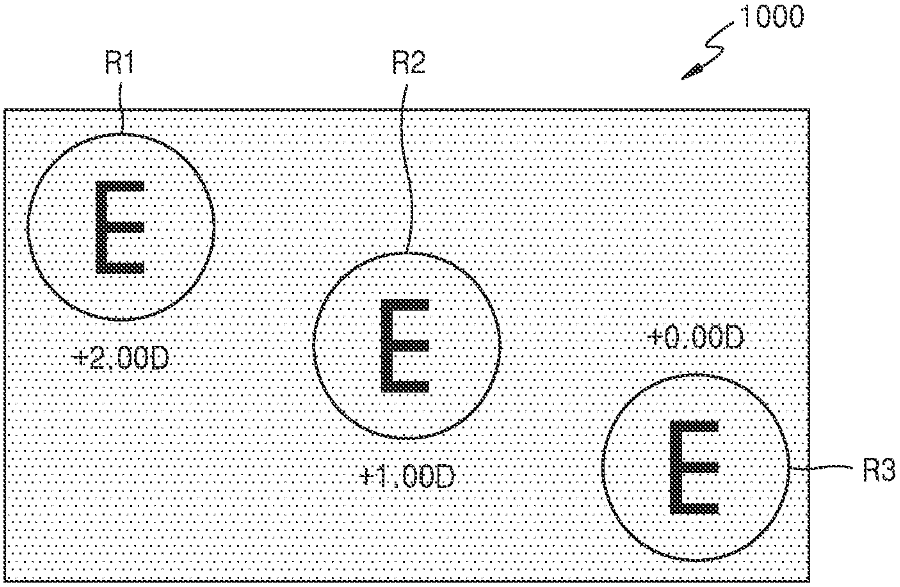
FIG. 22 is a diagram showing a VA measuring screen for measuring hyperopia according to an embodiment of the disclosure.
Figure 23:
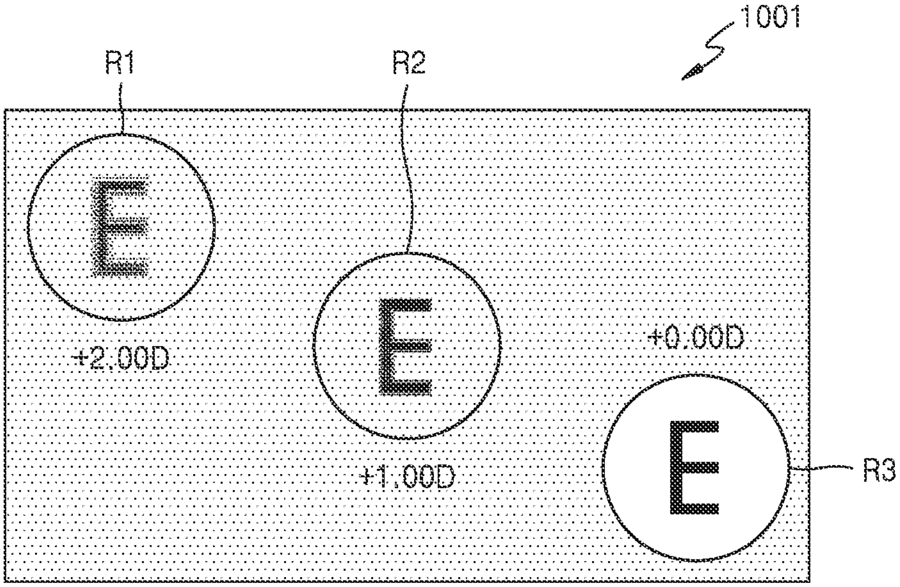
FIG. 23 is a diagram showing a VA measuring screen shown to a user having normal VA.
Figure 24:
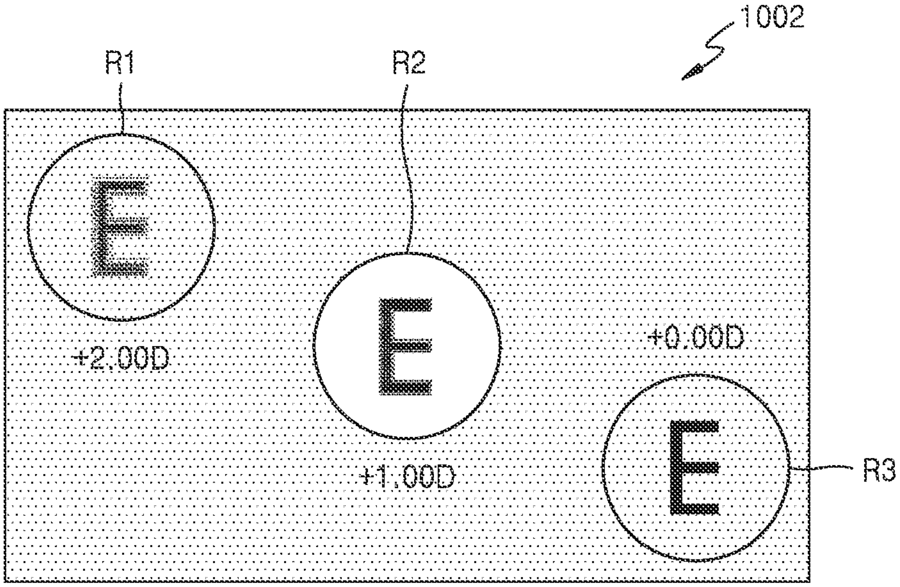
FIG. 24 is a diagram showing a VA measuring screen shown to a user having hyperopia.
Figure 25:
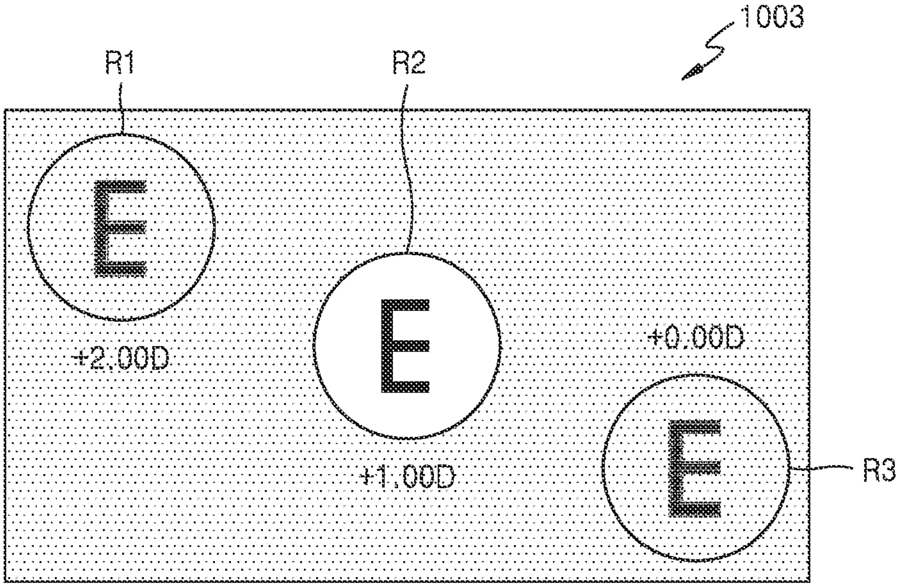
FIG. 25 is a diagram showing a VA measuring screen shown to a user having hyperopia and aged eyes.

FIG. 22 is a diagram showing a VA measuring screen 1000 for measuring hyperopia according to an embodiment of the disclosure, FIG. 23 is a diagram showing a VA measuring screen 1001 shown to a user having normal VA, FIG. 24 is a diagram showing a VA measuring screen 1002 shown to a user having hyperopia, and FIG. 25 is a diagram showing a VA measuring screen 1003 shown to a user having hyperopia and aged eyes.

Referring to FIG. 22, when hyperopia is measured, the display engines 110, 210, 510, 610, 710, and 810 may output light to show the VA measuring screen 1000 through the image combiners 120, 220, 520, and 620. In regions of the VA measuring screen 1000, which correspond to the first to third lens regions R1, R2, and R3, the same VA measuring image (e.g., a character 'E') may be displayed. The focus-tunable lenses 130, 530, 630, 730, and 830 may respectively assign different spherical lens powers (e.g., about +2.00 D, about +1.00 D, and about +0.00 D) to the first to third lens regions R1, R2, and R3.

A user having normal VA may most clearly see a VA measuring image of the third lens region R3 to which an optical power is not assigned, similar to the VA measuring screen 1001 shown in FIG. 23, and may abnormally see VA measuring images of the first and second lens regions R1 and R2 due to excessive refraction.

Hyperopic VA refers to a case in which an image of an object enters the eye and is focused behind the retina, and may be corrected by moving the focus on the eye through a convex lens. For example, a user having hyperopia (hereinafter, referred to as a user having VA of about +1.00 D) corrected by a spherical convex lens of about +1.00 D may most clearly see the VA measuring image of the second lens region R2 to which a spherical lens power of about +1.00 D is assigned, as in the VA measuring screen 1002 shown in FIG. 24. In addition, the VA measuring image of the third lens region R3 to which an optical power is not assigned may be regarded as an image at a relatively remote distance, such that a user having simple hyperopia may relatively clearly see the VA measuring image of the third lens region R3. The VA measuring image of the first lens region R1 may not be clearly shown to a user having hyperopia with VA of about +1.00 D due to excessive refraction.

Aged VA refers to a case where control of a crystalline lens is degraded. Thus, for a user having both hyperopia and aged eyes, correction is limited due to the aged eyes even when hyperopia is corrected by a convex lens. For example, as in the VA measuring screen 1003 shown in FIG. 25, a user having hyperopia with VA of about +1.00 D and aged eyes may clearly see the VA measuring image of the second lens region R2 to which a spherical lens power of about +1.00 D is assigned and may unclearly see the VA measuring images of the first and third lens region R1 and R3.

Similar to that shown in FIG. 24, for the VA measuring screen 1000 shown in FIG. 22, a user having VA of about +1.50 D may most clearly see the VA measuring image of the second lens region R2 to which a spherical lens optical lens of about +1.00 D is assigned and may clearly see the VA measuring image of the third lens region R3 to which an optical power is not assigned, but may not clearly see the VA measuring image of the first lens region R1 to which a spherical lens power of about +2.00 D is assigned. Thus, a user having VA of about +1.00 D and a user having VA of about +1.50 D may not be distinguished from each other merely with optical power arrangement as shown in FIG. 22, such that for more accurate VA measurement, additional fine measurement may be required.

Figure 26:
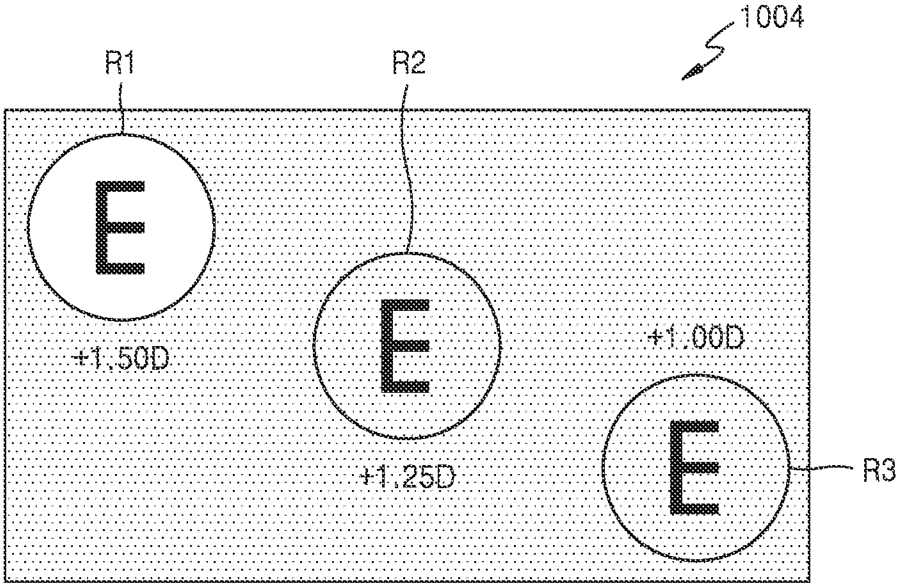
FIG. 26 is a diagram showing a VA measuring screen shown to a user having hyperopia in a fine measurement operation.
Figure 27:
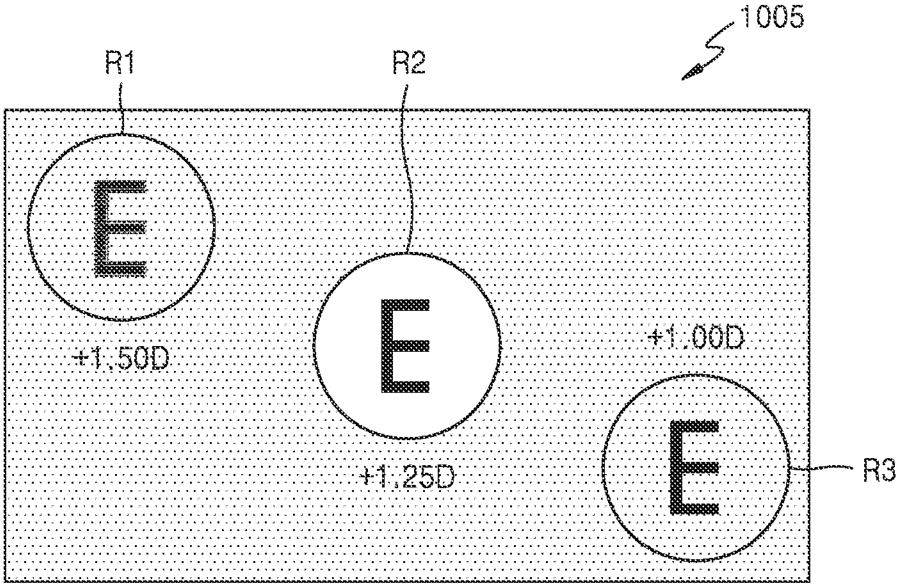
FIG. 27 is a diagram showing a VA measuring screen shown to a user having another hyperopia in a fine measurement operation.

FIG. 26 is a diagram showing a VA measuring screen 1004 shown to a user having hyperopia in a fine measurement operation, and FIG. 27 is a diagram showing a VA measuring screen 1005 shown to a user having another hyperopia in the fine measurement operation.

Referring to FIGS. 26 and 27, the same VA measuring image (e.g., the character 'E') is displayed in regions of the VA measuring screen 1004, which correspond to the first to third lens regions R1, R2, and R3, and changed optical powers are assigned to the first to third lens regions R1, R2, and R3 of the focus-tunable lenses 130, 230, 530, 630, 730, and 830. The changed optical powers may be changed based on an optical power specified in an existing measurement operation. For example, for the VA measuring screen 1000 shown in FIG. 22, when the user responds that the user may most clearly see the VA measuring image of the second lens region R2, an optical power to be changed may be changed based on an existing optical power (a spherical lens power of about +1.00 D in FIG. 22) that has been assigned to the selected second lens region R2. Moreover, differences among the optical powers assigned to the first to third lens regions R1, R2, and R3 may be less than differences among the existing optical powers. For example, in the example described with reference to FIG. 22, a difference between the optical powers is about 1.00 D, such that a difference between optical powers to be changed may be about 0.50 D or about 0.25 D. For example, spherical lens powers of about +1.50 D, about +1.25 D, and about +1.00 D may be respectively assigned to the first to third lens regions R1, R2, and R3. A user having VA of about +1.00 D may clearly see the VA measuring image of the third lens region R3 and may unclearly see the VA measuring images of the first and second lens regions R1 and R2. On the other hand, a user having VA of about +1.50 D may most clearly see the VA measuring image of the first lens region R1 and may also clearly see the VA measuring images of the second and third lens regions R2 and R3, as shown in FIG. 26. Thus, through a screen having optical power arrangement as shown in FIG. 26, VA of about +1.00 D and VA of about +1.50 D may be distinguished from each other. As shown in FIG. 27, a user having VA of about +1.25 D may most clearly see the VA measuring image of the second lens region R2 to which a spherical lens power of about +1.25 D is assigned and clearly see the VA measuring image of the third lens region R3 to which a spherical lens power of about +1.00 D is assigned, but may not clearly see the VA measuring image of the first lens region R1 to which a spherical lens power of about +1.50 D is assigned. Thus, VA of about +1.00 D, VA of about +1.25 D, and VA of about +1.50 D may be distinguished from one another through fine measurement.

Figure 28:
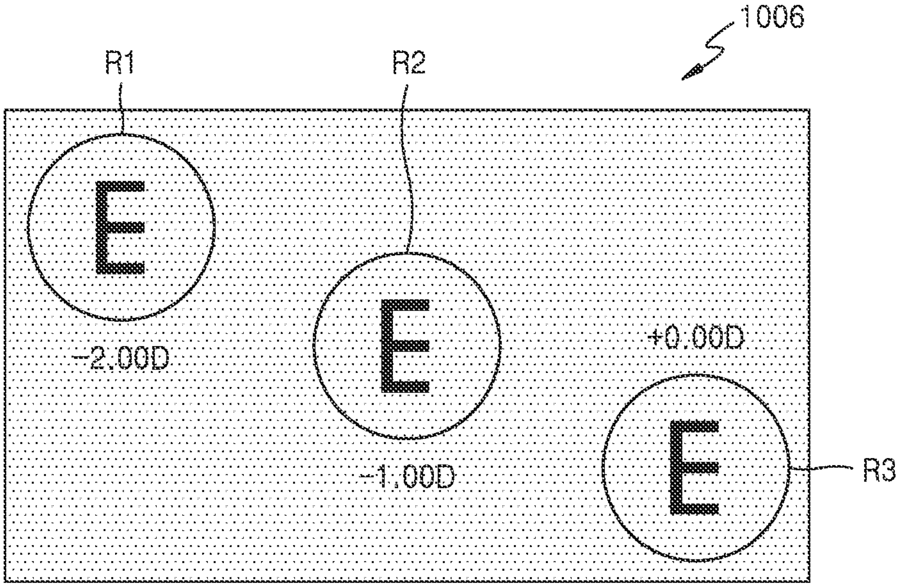
FIG. 28 is a diagram showing a VA measuring screen for measuring myopia according to an embodiment of the disclosure.
Figure 29:
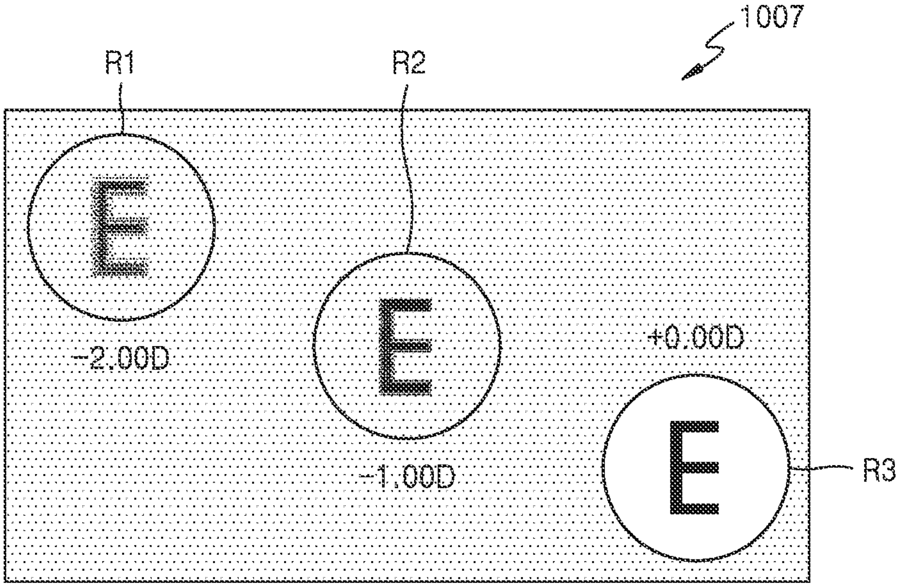
FIG. 29 is a diagram showing a VA measuring screen shown to a user having normal VA.
Figure 30:
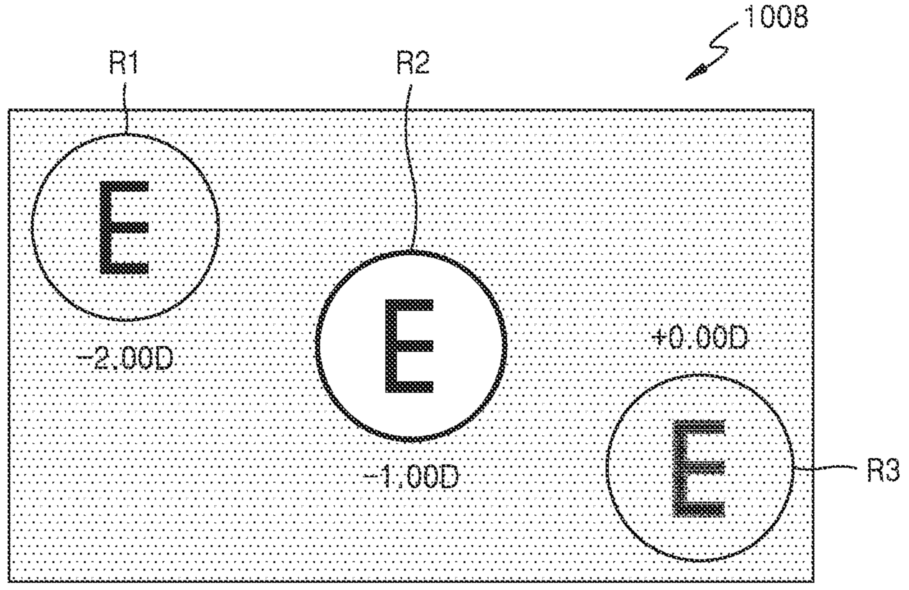
FIG. 30 is a diagram showing a VA measuring screen shown to a user having myopia.
Figure 31:
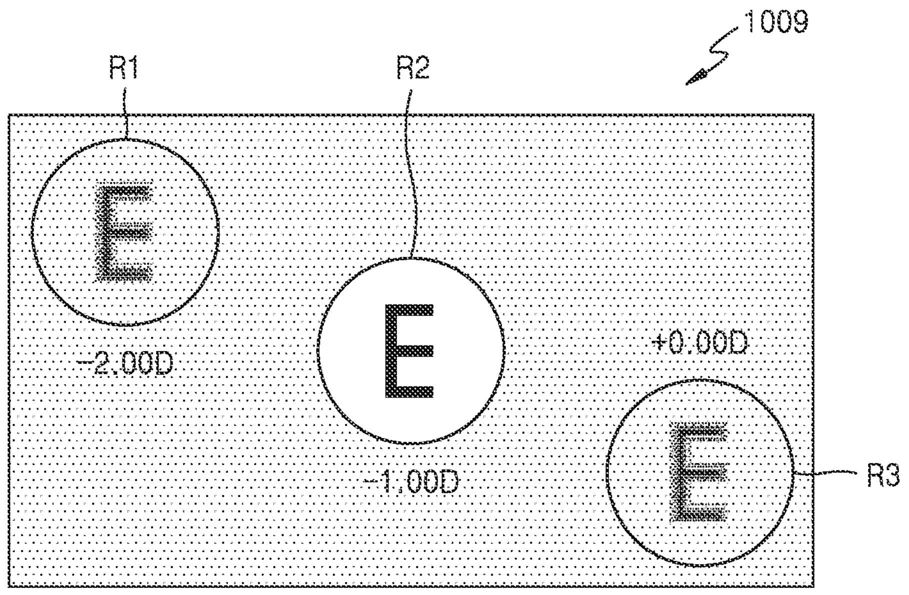
FIG. 31 is a diagram showing a VA measuring screen shown to a user having myopia and aged eyes.

FIG. 28 is a diagram showing a VA measuring screen 1006 for measuring hyperopia according to an embodiment of the disclosure, FIG. 29 is a diagram showing a VA measuring screen 1007 shown to a user having normal VA, FIG. 30 is a diagram showing a VA measuring screen 1008 shown to a user having hyperopia, and FIG. 31 is a diagram showing a VA measuring screen 1009 shown to a user having hyperopia and aged eyes.

Referring to FIG. 28, when myopia is measured, the display engines 110, 210, 510, 610, 710, and 810 may display the same VA measuring image (e.g., the character 'E') in regions of the VA measuring screen 1006, which correspond to the first to third lens regions R1, R2, and R3, and the focus-tunable lenses 130, 230, 530, 630, 730, and 830 may assign different spherical lens powers (e.g., about −2.00 D, about −1.00 D, and −0.00 D) to the first to third lens regions R1, R2, and R3.

As shown in FIG. 29, a user having normal VA may normally see the VA measuring image of the third lens region R3 to which an optical power is not assigned, and may abnormally see the VA measuring images of the first and second lens regions R1 and R2 due to excessive refraction.

Myopic VA refers to a case in which an image of an object enters the eye and is focused in front of the retina, and may be corrected by moving the focus on the eye through a concave lens. For example, a user having myopia (hereinafter, referred to as a user having VA of about −1.00 D) corrected by a spherical concave lens of about −1.00 D may most clearly see the VA measuring image of the second lens region R2 to which a spherical lens power of about −1.00 D is assigned, as shown in FIG. 30. A user having simple myopia may relatively clearly see an object at a relatively close distance. Thus, the user having simple myopia may also clearly see the VA measuring image of the first lens region R1 in which an image of the object is moved forward due to excessive refraction. The VA measuring image of the third lens region R3 to which an optical power is not assigned may be shown blurred to a user having myopia with VA of about −1.00 D.

For a user having both myopia and aged eyes, correction is limited due to the aged eyes even when myopia is corrected by a concave lens. For example, as shown in FIG. 31, a user having myopia with VA of about −1.00 D and aged eyes may normally see the VA measuring image of the second lens region R2 to which a spherical lens power of about −1.00 D is assigned and may unclearly see the VA measuring images of the first and third lens region R1 and R3.

For the VA measuring screen 1006 shown in FIG. 28, a user having VA of about −1.25 D may relatively clearly see the VA measuring image of the second lens region R2 to which a spherical lens power of about −1.00 D is assigned, and may not clearly see the VA measuring images of the first lens region R1 to which a spherical lens power of about −2.00 D is assigned and the third lens region R3 to which an optical power is not assigned. Thus, a user having VA of about −1.00 D and a user having VA of about −1.25 D may not be distinguished from each other merely with optical power arrangement as shown in FIG. 28, such that for more accurate VA measurement, additional fine measurement may be required.

Figure 32:
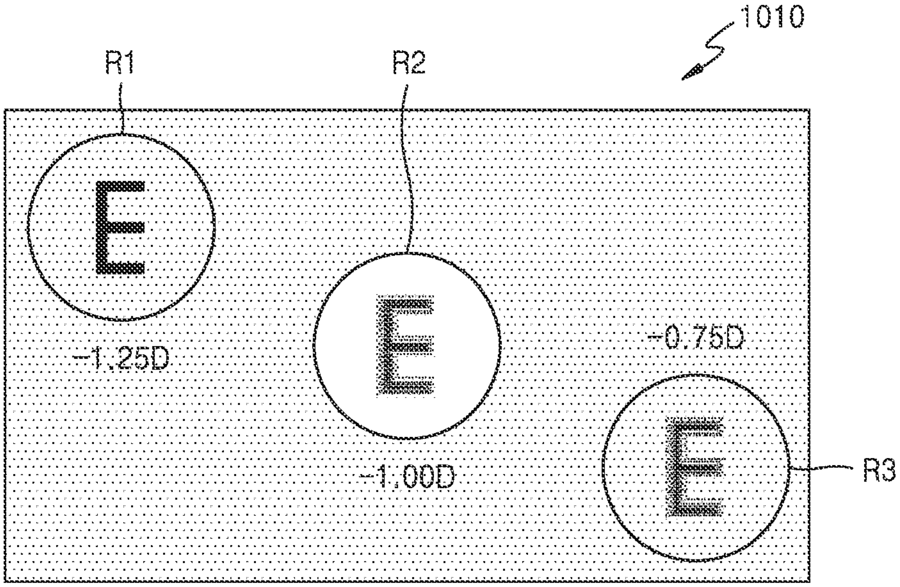
FIG. 32 is a diagram showing a VA measuring screen shown to a user having myopia in a fine measurement operation.

FIG. 32 is a diagram showing a VA measuring screen 1010 shown to a user having myopia in a fine measurement operation.

Referring to FIG. 32, the same VA measuring image (e.g., the character 'E') is displayed in regions of the VA measuring screen 1010, which correspond to the first to third lens regions R1, R2, and R3, and changed optical powers are assigned to the first to third lens regions R1, R2, and R3 of the focus-tunable lenses 130, 230, 530, 630, 730, and 830. The changed optical powers may be changed based on an optical power specified in an existing measurement operation. For example, for the VA measuring screen 1006 shown in FIG. 28, when the user responds that the user may most clearly see the VA measuring image of the second lens region R2, an optical power to be changed may be changed based on an existing optical power (a spherical lens power of about −1.00 D in FIG. 28) that has been assigned to the selected second lens region R2. Moreover, differences among the optical powers assigned to the first to third lens regions R1, R2, and R3 may be less than differences among the existing optical powers. For example, in the example described with reference to FIG. 28, a difference between the optical powers is about 1.00 D, such that a difference between optical powers to be changed may be about 0.50 D or about 0.25 D.

For example, spherical lens powers of about −1.25 D, about −1.00 D, and about −0.75 D may be respectively assigned to the first to third lens regions R1, R2, and R3. A user having VA of about −1.00 D may most clearly see the VA measuring image of the second lens region R2 and may also clearly see the VA measuring images of the first lens region R1, but may unclearly see the V measuring image of the third lens region R3. On the other hand, a user having VA of about −1.25 D may most clearly see the VA measuring image of the first lens region R1 and may unclearly see the VA measuring images of the second and third lens regions R2 and R3, as shown in FIG. 32. A user having VA of about −1.50 D may not clearly see all of the VA measuring images of the first to third lens regions R1, R2, and R3. Thus, through a screen having optical power arrangement as shown in FIG. 32, VA of about −1.00 D, VA of about −1.25 D, and VA of about −1.50 D may be distinguished from one another.

Figure 33:
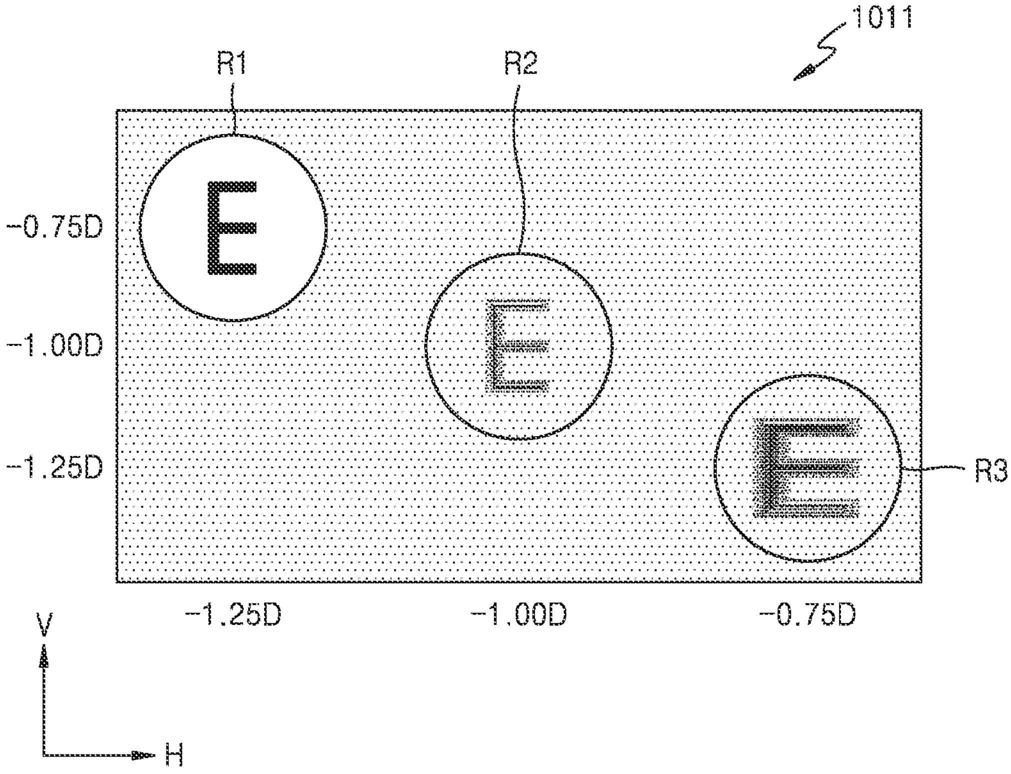
FIG. 33 is a diagram showing a VA measuring screen shown to a user having astigmatism.

FIG. 33 is a diagram showing a VA measuring screen shown 1011 to a user having astigmatism.

Referring to FIG. 33, when astigmatism is measured, the display engines 110, 210, 510, 610, 710, and 810 may display the same VA measuring image (e.g., the character 'E') in regions of the VA measuring screen 1011, which correspond to the first to third lens regions R1, R2, and R3, and the focus-tunable lenses 130, 230, 530, 630, 730, and 830 may assign different spherical lens powers having different axes to the first to third lens regions R1, R2, and R3.

A refractive error of astigmatism is usually accompanied by myopia or hyperopia, and thus before astigmatism is measured, myopia or hyperopia may be measured.

For example, a description will be made using a case where astigmatism is additionally measured in a state where VA of the user is measured as myopia of about −1.00 D. An optical power of about −0.75 D SPH/−0.50 D CYL at 90°, an optical power of about −1.00 D SPH, and an optical power of about −0.75 D SPH/−0.50 D CYL at 180° may be respectively assigned to the first, second, and third lens regions R1, R2, and R3 of the VA measuring screen 1011.

A refractive power distribution on the VA measuring screen 1011 may be implemented in a focus-tunable lens configured with the overlapping first and second strip electrode liquid crystal lenses 300 and 400 described with reference to FIG. 13. In an embodiment of the disclosure, an optical power assigned to the first lens region R1 may be given by a sum of a cylindrical lens power of about −1.25

D with the vertical direction V as an axis and a cylindrical lens power of about −0.75 D with the horizontal direction H as an axis (i.e., −0.75 D SPH/−0.50 D CYL at 90°), an optical power assigned to the second lens region R2 may be given by a sum of a cylindrical lens power of about −1.00 D with the vertical direction V as an axis and a cylindrical lens power of about −1.00 D with the horizontal direction H as an axis (i.e., −1.00 D SPH/−0.00 D CYL), and an optical power assigned to the third lens region R3 may be given by a sum of a cylindrical lens power of about −0.75 D with the vertical direction V as an axis and a cylindrical lens power of about −1.25 D with the horizontal direction H as an axis (i.e., −0.75 D SPH/−0.50 D CYL at 180°). A refractive power distribution on the VA measuring screen 1011 may also be implemented in the focus-tunable lens 530 implemented with the pixel electrode liquid crystal lens described with reference to FIG. 18.

A user without astigmatism may most clearly see the VA measuring image of the second lens region R2 to which a spherical lens power is assigned, and may not clearly see the VA measuring images of the first and third lens regions R1 and R3 due to a cylindrical lens power. However, when VA of a user has an astigmatism angle of about 90°, the VA measuring image of the first lens region R1 to which an optical power of about −0.75 D SPH/−0.50 D CYL at 90° is assigned may be clearly visible to the user, and the VA measuring images of the second and third lens regions R2 and R3 may not be clearly visible. When VA of a user has an astigmatism angle of about 180°, the VA measuring image of the third lens region R3 to which an optical power of about −0.75 D SPH/−0.50 D CYL at 180° is assigned may be clearly visible to the user, and the VA measuring images of the first and second lens regions R1 and R2 may not be clearly visible.

Thus, through optical power arrangement shown in FIG. 33, VA including an astigmatism angle of the user may be measured.

Figure 34:
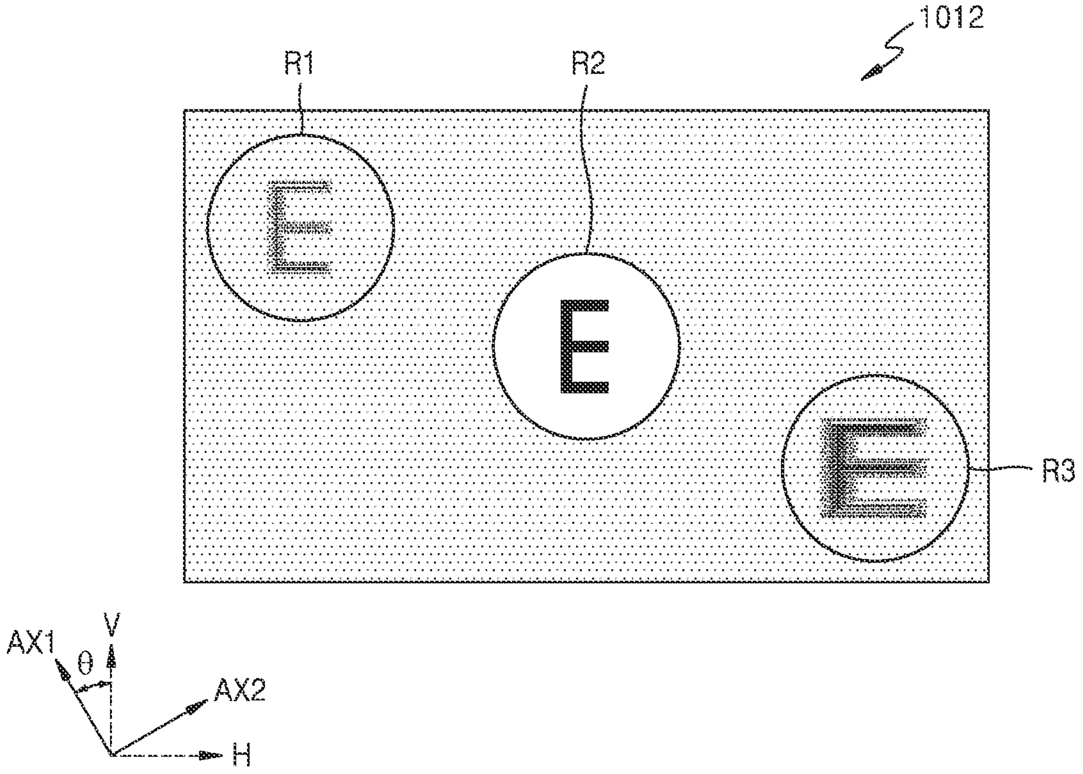
FIG. 34 is a diagram showing a VA measuring screen shown to a user having astigmatism in a fine measurement operation.

When an astigmatism direction of the user is about 80° or 110°, the VA measuring image of the first lens region R1 may be more clearly visible than those of the second and third lens region R2 and R3, such that the user's astigmatism direction needs to be finely measured. As in the example described with reference to FIG. 18, the focus-tunable lens 530 implemented with the pixel electrode liquid crystal lens may more freely adjust an axial direction of the cylindrical lens power, enabling fine measurement of astigmatism. FIG. 34 is a diagram showing a VA measuring screen 1012 shown to a user having astigmatism in a fine measurement operation. For example, by changing an angle 8 of the axial direction of the cylindrical lens power with respect to the first to third lens regions R1, R2, and R3 to 110°, 0°, and 20°, an astigmatism angle of the user may be more accurately measured.

When the apparatuses 100, 200, 500, 600, 700, and 800 according to the above-described embodiments of the disclosure are AR glasses, the processor 170 may provide a processor for measuring VA of a user by driving a VA measuring module to the user, and drive a VA correcting module based on a the measured VA to provide an optical power for the focus-tunable lenses 130, 230, 530, 630, 730, and 830 to correct a user's refraction error, thereby providing use convenience to the user.

Next, a method of measuring VA using the apparatuses 100, 200, 500, 600, 700, and 800 according the above-described embodiments of the disclosure will be described.

Figure 35:
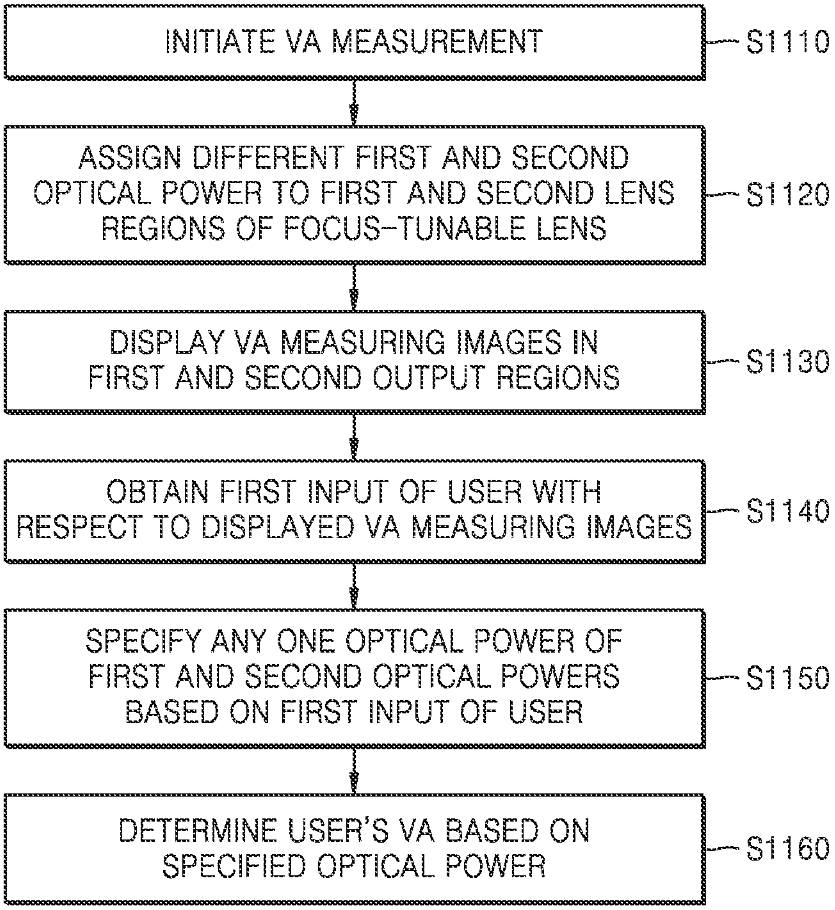
FIG. 35 is a flowchart of a method of measuring a VA according to an embodiment of the disclosure.

FIG. 35 is a flowchart of a method of measuring VA according to an embodiment of the disclosure. Referring to FIG. 35, when the user selects VA measurement after wearing the apparatuses 100, 200, 500, 600, 700, and 800, then the processor 170 may load a VA measuring module from the storage 160 to initiate VA measurement, in operation S1110.

The processor 170 may respectively assign different first and second optical powers to first and second lens regions of the focus-tunable lenses 130, 230, 530, 630, 730, and 830 in operation S1120, and display VA measuring images through first and second output regions of the image combiners 120, 220, 520, and 620, which correspond to the first and second lens regions, through the display engines 110, 210, 510, 610, 710, and 810, in operation S1130. The processor 170 may provide, to the user, a process of changing settings for the first and second optical powers or settings for a size and a shape of the VA measuring image. The first and second optical powers to be assigned may include a positive (+) spherical lens power, a negative (−) spherical lens power, or a cylindrical lens power. Information about the first and second optical powers to be assigned or the VA measuring image may be previously stored in the storage 160. The number of lens regions of the focus-tunable lenses 130, 230, 530, 630, 730, and 830 may be greater than or equal to 3.

The processor 170 may guide the user to select a clearly visible one of displayed VA measuring images and obtain information (a first input) about user's selection, in operation S1140. A guiding scheme may be implemented with, but not limited to, a text on a screen or voice through a speaker.

In an embodiment of the disclosure, the processor 170 may guide the user to select the most clearly visible VA measuring image.

In an embodiment of the disclosure, the processor 170 may guide the user to select a clearly visible VA measuring image and allow the user to select two or more images.

The processor 170 may specify an optical power assigned to a lens region corresponding to an output region where the most clearly visible VA measuring image is displayed based on the user's first input in operation S1150, and determine user's VA based on the specified optical power in operation S1160. For example, when an optical power assigned to a lens region corresponding to an output region where the most clearly visible VA measuring image is displayed is about +1.00 D SPH, the user may be determined to have hyperopia of about +1.00 D.

Such VA measurement may be performed repeatedly a plurality of times. When the optical power is specified based on the user's first input as described with reference to FIG. 35 in operation S1150, a finely measuring process may be performed in place of operation S1160 of determining the user's VA based on the specified optical power. When the user selects two or more clearly visible VA measuring images, a process of specifying an optical power at random based on any one of them and finely measuring the VA based on the specified optical power may be performed.

Figure 36:
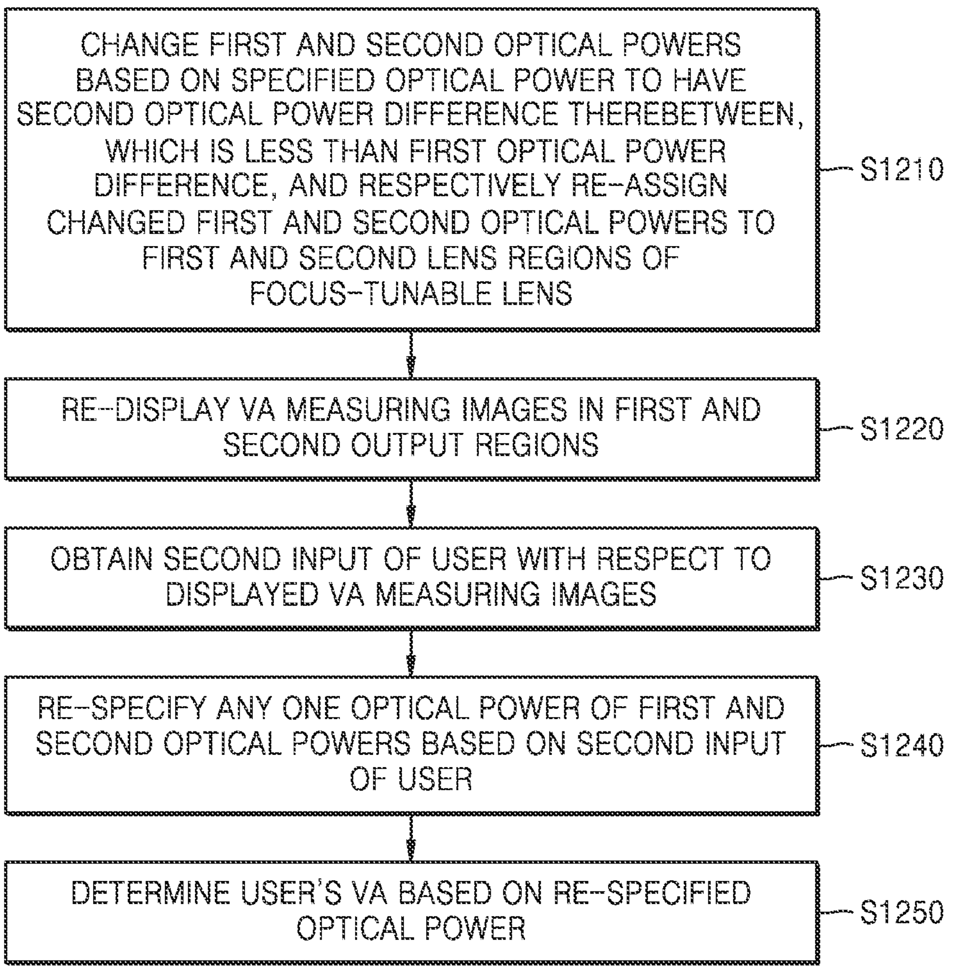
FIG. 36 is a flowchart of a method of measuring a VA according to an embodiment of the disclosure.

FIG. 36 is a flowchart of a method of measuring VA according to an embodiment of the disclosure. Referring to FIG. 36, the processor 170 may change first and second optical powers based on the specified optical power and re-assign the changed first and second optical powers to the first and second lens regions of the focus-tunable lenses 130, 230, 530, 630, 730, and 830 in operation S1210, and re-display VA measuring images through output regions corresponding to the first and second lens regions in operation S1220. Any one of the changed first and second optical powers may be a specified optical power. A difference between the changed first and second optical powers may be set less than a difference between the first and second optical powers before changed.

Next, the processor 170 may guide the user to select the most clearly visible one of the re-displayed VA measuring images and obtain information (a second input) about user's selection, in operation S1230.

The processor 170 may re-specify again an optical power assigned to a lens region corresponding to an output region where the most clearly visible VA measuring image is displayed based on the user's second input in operation S1240, and determine user's VA based on the re-specified optical power in operation S1250.

Figure 37:
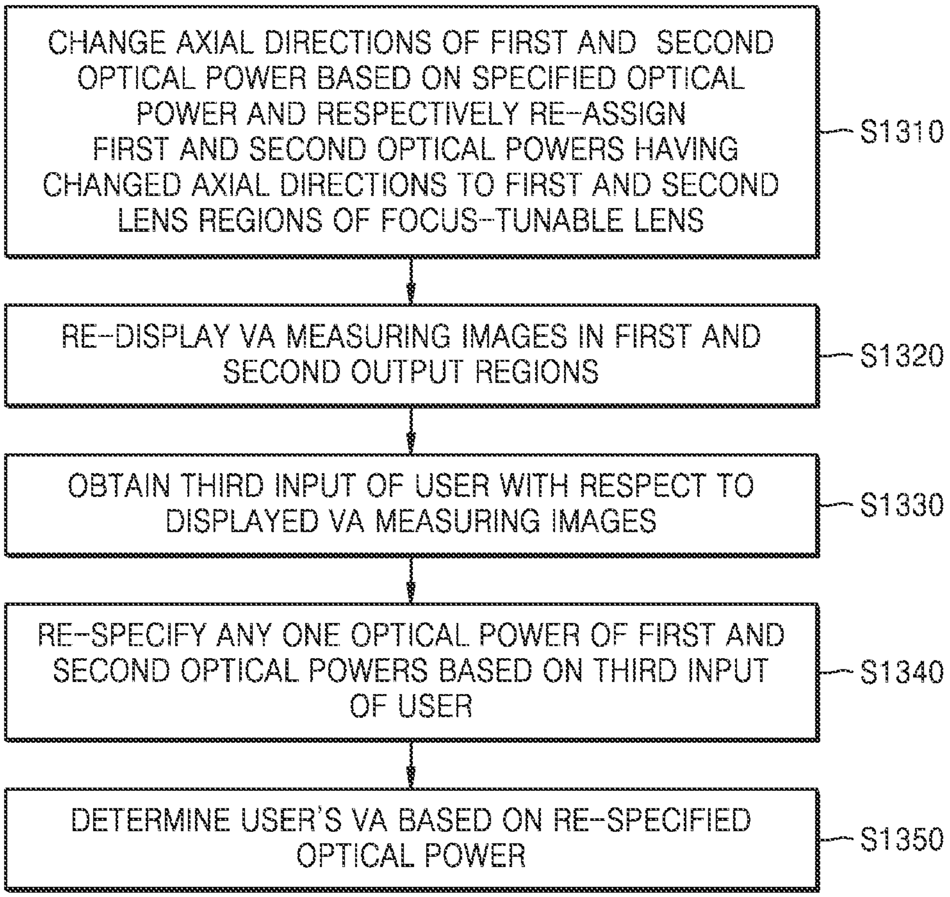
FIG. 37 is a flowchart of a method of measuring a VA according to an embodiment of the disclosure.

Astigmatism may be measured after myopia or hyperopia is measured. For example, after myopia or hyperopia is measured through a VA measurement method described above with reference to FIGS. 35 and 36, astigmatism may be additionally measured. FIG. 37 is a flowchart of a method of measuring VA according to an embodiment of the disclosure. Referring to FIG. 37, the processor 170 may change axial directions of first and second optical powers based on the optical power specified in a previous operation and re-assign the first and second optical powers having the changed axial directions to the first and second lens regions of the focus-tunable lenses 130, 230, 530, 630, 730, and 830 in operation S1310, and re-display VA measuring images in the first and second lens regions in operation S1320. The changed first and second optical powers may have axial directions changed in a range of 0 degree to 90 degrees based on the optical power specified in operation S1150 of FIG. 35 or in operation S1240 of FIG. 36. For example, the optical power specified in the previous operation may be about −1.00 D SPH. In this case, the changed first optical power may be about −0.75 D SPH, 0.50 CYL at 90°, and the changed second optical power may be about −0.75 D SPH, 0.50 CYL at 180°. In the focus-tunable lenses 130, 230, 530, 630, 730, and 830, a third lens region to which an optical power of about −1.00 D SPH is assigned or a lens region to which an optical power of other axes is assigned may be additionally provided.

Next, the processor 170 may guide the user to select the most clearly visible one of the re-displayed VA measuring images and obtain information (a third input) about user's selection, in operation S1330. The processor 170 may re-specify again an optical power assigned to a lens region corresponding to an output region where the most clearly visible VA measuring image is displayed based on the user's third input in operation S1340, and determine user's astigmatism VA based on the re-specified optical power in operation S1350.

Astigmatism measurement may be repeated a plurality of times. For example, instead of operation S1350, the processor 170 may go back to operation S1310 to re-change the axial direction of the optical power based on the re-specified optical power and repeat astigmatism measurement to more accurately measure the astigmatism direction of the user. When the user selects two or more clearly visible VA measuring images, an optical power may be specified at random based on any one of them, the axial direction of the optical power may be re-changed based on the specified optical power, and astigmatism measurement may be repeated.

Existing subjective refraction may perform VA measurement in which the user sees VA measuring images by sequentially using test refractive lenses having different optical powers and selects the test refractive lens showing a clear image. In this scheme, the user has to memorize and compare clarities of images in the previous operation, such that the user may often find it difficult to compare the clarities. On the other hand, as described above, the embodiment of the disclosure show VA measuring images to which different optical powers are reflected, on one screen at a time, such that the user may simultaneously compare the VA measuring images to which different optical powers are reflected, and thus may more easily make selection.

An embodiment of the disclosure may be implemented using a recording medium including a computer-executable instruction such as a computer-executable programming module. A computer-readable recording medium may be an available medium that is accessible by a computer, and includes all of a volatile medium, a non-volatile medium, a separated medium, and a non-separated medium. The computer-readable recording medium may also include a computer storage medium and a communication medium. The computer storage medium includes all of a volatile medium, a non-volatile medium, a separated medium, and a non-separated medium, which is implemented by a method or technique for storing information such as a computer-readable instruction, a data structure, a programming module, or other data. A communication medium may typically include a computer-readable instruction, a data structure, or other data of a modulated data signal such as a programming module.

The computer-readable storage medium may be provided in the form of a non-transitory storage medium. When the storage medium is 'non-transitory', it means that the storage medium is tangible and does not include signals (e.g., electromagnetic waves), and it does not limit that data is semi-permanently or temporarily stored in the storage medium. For example, the 'non-transitory storage medium' may include a buffer storing data temporarily.

According to an embodiment of the disclosure, a method according to various embodiments of the disclosure may be included and provided in a computer program product. The computer program product may be traded as a product between a seller and a buyer. The computer program product may be distributed in the form of a machine-readable storage medium (e.g., compact disc read only memory (CD-ROM)), or be distributed (e.g., downloaded or uploaded) online via an application store (e.g., Play Store™), or between two user devices (e.g., smart phones) directly. When distributed online, at least a part of the computer program product (e.g., a downloadable app) may be temporarily generated or at least temporarily stored in the machine-readable storage medium, such as memory of the manufacturer's server, a server of the application store, or a relay server.

In the specification, the term "unit" may be a hardware component such as a processor or a circuit, and/or a software component executed by a hardware component like a processor.

Those of ordinary skill in the art to which the disclosure pertains will appreciate that the disclosure may be implemented in different detailed ways without departing from the technical spirit or essential characteristics of the disclosure. Accordingly, the aforementioned embodiments of the disclosure should be construed as being only illustrative, but should not be constructed as being restrictive from all aspects. For example, each element described as a single type may be implemented in a distributed manner, and likewise, elements described as being distributed may be implemented as a coupled type.

According to the disclosure, an apparatus and method for measuring a visual acuity (VA) may improve convenience of VA measurement by using a focus-tunable lens.

According to the disclosure, an apparatus and method for measuring a VA may provide a VR/AR device configured to autonomously measure the VA.

According to the disclosure, an apparatus and method for measuring a VA may provide an immersive VR/AR environment by providing VA correction to a VR/AR device.

While the apparatus and method for measuring VA by using a focus-tunable lens according to the disclosure has been shown and described in connection with the embodiments to help understanding of the disclosure, it will be apparent to those of ordinary skill in the art that modifications and variations may be made. Therefore, the true technical scope of the disclosure should be defined by the appended claims and their equivalents.

What is claimed is:

1. An apparatus configured to measure a visual acuity (VA) by a focus-tunable lens, the apparatus comprising:

a display engine configured to project light comprising a VA measuring image;

an image combiner configured to guide the light projected from the display engine;

the focus-tunable lens provided on a path of the light guided by the image combiner;

an input device configured to receive a user's input with respect to the VA measuring image;

a storage configured to store one or more instructions; and a processor configured to execute the one or more instructions to:

control the focus-tunable lens to assign a first optical power to a first lens region and a second optical power that is different from the first optical power to a second lens region, the first lens region and the second lens region being included in a lens surface of the focus-tunable lens;

control the display engine to display the VA measuring image through a first output region and a second output region of the image combiner, which respectively correspond to the first lens region and the second lens region of the focus-tunable lens;

control the input device to receive the user's input;

specify one optical power of the first optical power and the second optical power based on the user's input; and determine a VA of a user based on the specified optical power, wherein the focus-tunable lens comprises a first liquid crystal lens comprising a first strip electrode array and divided into a plurality of first zones, and a second liquid crystal lens comprising a second strip electrode array and divided into a plurality of second zones, wherein the first strip electrode array comprises a plurality of first strip electrodes having a linear shape extending along a first direction, and the second strip electrode array comprises a plurality of second strip electrodes having a linear shape extending along a second direction perpendicular to the first direction, wherein the plurality of first strip electrodes and the plurality of second strip electrodes overlap each other orthogonally, wherein the processor is further configured to assign the first optical power to the first lens region by setting a first voltage profile applied to at least one first strip electrode included in a first zone among the plurality of first zones corresponding to the first lens region and at least one second strip electrode included in a second zone among the plurality of second zones corresponding to the first lens region, and assign the second optical power to the second lens region by setting a second voltage profile applied to at least one first strip electrode included in a first zone among the plurality of first zones corresponding to the second lens region and at least one second strip electrode included in a second zone among the plurality of second zones corresponding to the second lens region, wherein the first optical power has a first cylindrical lens optical power with the first direction, placed on the lens surface of the focus-tunable lens, as an axial direction, and the second optical power has a second cylindrical lens optical power with the second direction, placed on the lens surface of the focus-tunable lens and orthogonal to the first direction, as the axial direction based on measuring astigmatism of the user, and wherein the measuring of the VA of the user comprises determining an astigmatism direction of the user based on the axial direction of each of the first cylindrical lens optical power and the second cylindrical lens optical power.

2. The apparatus of claim 1, wherein a first VA measuring image displayed through the first output region and a second VA measuring image displayed through the second output region are same images having same sizes.

3. The apparatus of claim 1, wherein the focus-tunable lens comprises a pixel electrode liquid crystal lens comprising a pixel electrode array, and wherein the processor is further configured to:

apply a voltage to first pixel electrodes of the pixel electrode array, which pass by the first lens region, such that the first lens region has the first optical power; and apply a voltage to second pixel electrodes of the pixel electrode array, which pass by the second lens region, such that the second lens region has the second optical power.

4. The apparatus of claim 1, wherein the input device comprises at least one of a gaze tracking sensor, a microphone, a button, and a gesture recognition sensor.

5. The apparatus of claim 1, wherein the image combiner is further configured to guide the light projected from the display engine to a target region and project light of a real scene, and wherein the focus-tunable lens is provided on a path of the light guided from the image combiner to the target region.

6. The apparatus of claim 5, wherein the image combiner comprises one of a waveguide, multiple mirrors, and a reflective mirror.

7. The apparatus of claim 1, wherein information with respect to the measured VA of the user is stored in the storage.

8. The apparatus of claim 1, wherein the apparatus comprises an augmented reality (AR) device.

9. A method of measuring a visual acuity (VA) by a focus-tunable lens, the method comprising:

assigning a first optical power to a first lens region and a second optical power that is different from the first optical power to a second lens region, the first lens region and the second lens region being included on a lens surface of the focus-tunable lens;

displaying a VA measuring image through a first output region and a second output region of an image combiner, which respectively correspond to the first lens region and the second lens region of the focus-tunable lens;

receiving a first input of a user with respect to the VA measuring image;

specifying one optical power of the first optical power and the second optical power based on the first input of the user; and determining a VA of the user based on the specified optical power, wherein the focus-tunable lens comprises a first liquid crystal lens comprising a first strip electrode array and divided into a plurality of first zones, and a second liquid crystal lens comprising a second strip electrode array and divided into a plurality of second zones, wherein the first strip electrode array comprises a plurality of first strip electrodes having a linear shape extending along a first direction, and the second strip electrode array comprises a plurality of second strip electrodes having a linear shape extending along a second direction perpendicular to the first direction, wherein the plurality of first strip electrodes and the plurality of second strip electrodes overlap each other orthogonally, wherein method further comprises:

assigning the first optical power to the first lens region by setting a first voltage profile applied to at least one first strip electrode included in a first zone among the plurality of first zones corresponding to the first lens region and at least one second strip electrode included in a second zone among the plurality of second zones corresponding to the first lens region; and assigning the second optical power to the second lens region by setting a second voltage profile applied to at least one first strip electrode included in a first zone among the plurality of first zones corresponding to the second lens region and at least one second strip electrode included in a second zone among the plurality of second zones corresponding to the second lens region, wherein the assigning of the first optical power and the second optical power to the focus-tunable lens comprises applying a voltage to electrodes of the focus-tunable lens such that the first optical power has a first cylindrical lens optical power with the first direction, placed on the lens surface of the focus-tunable lens, as an axial direction, and the second optical power has a second cylindrical lens optical power with the second direction, placed on the lens surface of the focus-tunable lens and orthogonal to the first direction, as the axial direction based on measuring astigmatism of the user, and wherein the measuring of the VA of the user comprises determining an astigmatism direction of the user based on the axial direction of each of the first cylindrical lens optical power and the second cylindrical lens optical power.

10. The method of claim 9, wherein a first VA measuring image displayed through the first output region and a second VA measuring image displayed through the second output region are same images having same sizes.

11. The method of claim 9, further comprising:

changing the first optical power and the second optical power based on the specified optical power and re-assigning the changed first optical power and the changed second optical power to the focus-tunable lens;

displaying the VA measuring image and receiving a second input of the user;

re-specifying one optical power of the changed first optical power and the changed second optical power based on the second input of the user; and determining the VA of the user based on the re-specified optical power.

12. The method of claim 9, further comprising:

after changing the first direction in a range of greater than 0 degree to 90 degree, assigning the changed first optical power and the second optical power to the focus-tunable lens;

displaying the VA measuring image;

receiving a third input of the user;

re-specifying one optical power of the changed first optical power and the changed second optical power based on the third input of the user; and re-measuring the VA of the user based on the re-specified optical power.

13. The method of claim 9, wherein the first input of the user is input by at least one of a gaze tracking sensor, a microphone, a button, and a gesture recognition sensor.

14. The method of claim 9, further comprising storing the measured VA of the user in a storage of an apparatus.

15. A non-transitory computer-readable recording medium for executing a method of measuring a visual acuity (VA) by a focus-tunable lens on a computer, the method comprising:

assigning a first optical power to a first lens region and a second optical power that is different from the first optical power to a second lens region, the first lens region and the second lens region being included on a lens surface of the focus-tunable lens;

displaying a VA measuring image through a first output region and a second output region of an image combiner, which respectively correspond to the first lens region and the second lens region of the focus-tunable lens;

receiving a first input of a user with respect to the VA measuring image;

specifying one optical power of the first optical power and the second optical power based on the first input of the user; and determining a VA of the user based on the specified optical power, wherein the focus-tunable lens comprises a first liquid crystal lens comprising a first strip electrode array and divided into a plurality of first zones, and a second liquid crystal lens comprising a second strip electrode array and divided into a plurality of second zones, wherein the first strip electrode array comprises a plurality of first strip electrodes having a linear shape extending along a first direction, and the second strip electrode array comprises a plurality of second strip electrodes having a linear shape extending along a second direction perpendicular to the first direction, wherein the plurality of first strip electrodes and the plurality of second strip electrodes overlap each other orthogonally, wherein method further comprises:

assigning the first optical power to the first lens region by setting a first voltage profile applied to at least one first strip electrode included in a first zone among the plurality of first zones corresponding to the first lens region and at least one second strip electrode included in a second zone among the plurality of second zones corresponding to the first lens region; and assigning the second optical power to the second lens region by setting a second voltage profile applied to at least one first strip electrode included in a first zone among the plurality of first zones corresponding to the second lens region and at least one second strip electrode included in a second zone among the plurality of second zones corresponding to the second lens region, wherein the assigning of the first optical power and the second optical power to the focus-tunable lens comprises applying a voltage to electrodes of the focus-tunable lens such that the first optical power has a first cylindrical lens optical power with the first direction, placed on the lens surface of the focus-tunable lens, as an axial direction, and the second optical power has a second cylindrical lens optical power with the second direction, placed on the lens surface of the focus-tunable lens and orthogonal to the first direction, as the axial direction based on measuring astigmatism of the user, and wherein the measuring of the VA of the user comprises determining an astigmatism direction of the user based on the axial direction of each of the first cylindrical lens optical power and the second cylindrical lens optical power.

* * * * *